United States Patent
Bae et al.

(10) Patent No.: US 9,631,481 B1
(45) Date of Patent: Apr. 25, 2017

(54) SEMICONDUCTOR DEVICE INCLUDING LEADFRAME WITH A COMBINATION OF LEADS AND LANDS AND METHOD

(71) Applicant: AMKOR TECHNOLOGY, INC., Tempe, AZ (US)

(72) Inventors: Jae Min Bae, Seoul (KR); Byong Jin Kim, Kyunggi-do (KR); Won Bae Bang, Seoul (KR)

(73) Assignee: Amkor Technology, Inc., Tempe, AZ (US)

( * ) Notice: Subject to any disclaimer, the term of this patent is extended or adjusted under 35 U.S.C. 154(b) by 0 days.

(21) Appl. No.: 15/293,524

(22) Filed: Oct. 14, 2016

Related U.S. Application Data

(63) Continuation of application No. 14/983,938, filed on Dec. 30, 2015, which is a continuation of application
(Continued)

(51) Int. Cl.
*H01L 33/62* (2010.01)
*E21B 47/10* (2012.01)
(Continued)

(52) U.S. Cl.
CPC .......... *E21B 47/101* (2013.01); *E21B 21/08* (2013.01); *E21B 49/005* (2013.01); *G01N 29/024* (2013.01)

(58) Field of Classification Search
CPC ....... H01L 2924/00; H01L 2224/48247; H01L 2224/73265; H01L 2224/32245;
(Continued)

(56) References Cited

U.S. PATENT DOCUMENTS

| 2,596,993 A | 5/1952 | Gookin |
| 3,435,815 A | 4/1969 | Forcier |

(Continued)

FOREIGN PATENT DOCUMENTS

| DE | 19734794 A1 | 8/1997 |
| EP | 0393997 | 10/1990 |

(Continued)

OTHER PUBLICATIONS

National Semiconductor Corporation, "Leadless Leadframe Package," Informational Pamphlet from webpage, 21 pages, Oct. 2002, www.national.com.
(Continued)

*Primary Examiner* — Stephen W Smoot
*Assistant Examiner* — Edward Chin
(74) *Attorney, Agent, or Firm* — Kevin B. Jackson

(57) ABSTRACT

A semiconductor device includes a die pad, a plurality of first lands each having a first land first top recessed portion disposed on a first land first end distal to the die pad, and a plurality of second lands each having a second land first bottom recessed portion disposed on a second land first end distal to the die pad. A semiconductor die is electrically connected to the first and second lands. A package body, which defines a bottom surface and a side surface, at least partially encapsulating the first and second lands and the semiconductor die such that at least portions of the first and second lands are exposed in and substantially flush with the bottom surface of the package body.

20 Claims, 11 Drawing Sheets

Related U.S. Application Data

No. 14/106,139, filed on Dec. 13, 2013, now Pat. No. 9,275,939, which is a continuation of application No. 13/015,071, filed on Jan. 27, 2011, now Pat. No. 8,648,450.

(51) Int. Cl.
  *G01N 29/024* (2006.01)
  *E21B 49/00* (2006.01)
  *E21B 21/08* (2006.01)

(58) Field of Classification Search
  CPC . H01L 2224/49109; H01L 2224/48091; H01L 2924/00014; H01L 2224/49171; H01L 2924/15747; H01L 2224/32225; H01L 2224/48465
  See application file for complete search history.

(56) References Cited

U.S. PATENT DOCUMENTS

| | | |
|---|---|---|
| 3,734,660 A | 5/1973 | Davies et al. |
| 3,838,984 A | 10/1974 | Crane et al. |
| 4,054,238 A | 10/1977 | Lloyd et al. |
| 4,189,342 A | 2/1980 | Kock |
| 4,221,925 A | 9/1980 | Finley et al. |
| 4,258,381 A | 3/1981 | Inaba |
| 4,289,922 A | 9/1981 | Devlin |
| 4,301,464 A | 11/1981 | Otsuki et al. |
| 4,332,537 A | 6/1982 | Slepcevic |
| 4,417,266 A | 11/1983 | Grabbe |
| 4,451,224 A | 5/1984 | Harding |
| 4,530,152 A | 7/1985 | Roche et al. |
| 4,541,003 A | 9/1985 | Otsuka et al. |
| 4,646,710 A | 3/1987 | Schmid et al. |
| 4,707,724 A | 11/1987 | Suzuki et al. |
| 4,727,633 A | 3/1988 | Herrick |
| 4,737,839 A | 4/1988 | Burt |
| 4,756,080 A | 7/1988 | Thorp, Jr. et al. |
| 4,812,896 A | 3/1989 | Rothgery et al. |
| 4,862,245 A | 8/1989 | Pashby et al. |
| 4,862,246 A | 8/1989 | Masuda et al. |
| 4,907,067 A | 3/1990 | Derryberry |
| 4,920,074 A | 4/1990 | Shimizu et al. |
| 4,935,803 A | 6/1990 | Kalfus et al. |
| 4,942,454 A | 7/1990 | Mori et al. |
| 4,987,475 A | 1/1991 | Sclesinger et al. |
| 5,018,003 A | 5/1991 | Yasunaga |
| 5,029,386 A | 7/1991 | Chao et al. |
| 5,041,902 A | 8/1991 | McShane |
| 5,057,900 A | 10/1991 | Yamazaki |
| 5,059,379 A | 10/1991 | Tsutsumi et al. |
| 5,065,223 A | 11/1991 | Matsuki et al. |
| 5,070,039 A | 12/1991 | Johnson et al. |
| 5,087,961 A | 2/1992 | Long et al. |
| 5,091,341 A | 2/1992 | Asada et al. |
| 5,096,852 A | 3/1992 | Hobson et al. |
| 5,118,298 A | 6/1992 | Murphy |
| 5,122,860 A | 6/1992 | Kikuchi et al. |
| 5,134,773 A | 8/1992 | LeMaire et al. |
| 5,151,039 A | 9/1992 | Murphy |
| 5,157,475 A | 10/1992 | Yamaguchi |
| 5,157,480 A | 10/1992 | McShane et al. |
| 5,168,368 A | 12/1992 | Gow, 3rd et al. |
| 5,172,213 A | 12/1992 | Zimmerman |
| 5,172,214 A | 12/1992 | Casto |
| 5,175,060 A | 12/1992 | Enomoto et al. |
| 5,200,362 A | 4/1993 | Lin et al. |
| 5,200,809 A | 4/1993 | Kwon |
| 5,214,845 A | 6/1993 | King et al. |
| 5,216,278 A | 6/1993 | Lin et al. |
| 5,218,231 A | 6/1993 | Kudo |
| 5,221,642 A | 6/1993 | Burns |
| 5,250,841 A | 10/1993 | Sloan et al. |
| 5,252,853 A | 10/1993 | Michii |
| 5,258,094 A | 11/1993 | Furui et al. |
| 5,266,834 A | 11/1993 | Nishi et al. |
| 5,273,938 A | 12/1993 | Lin et al. |
| 5,277,972 A | 1/1994 | Sakumoto et al. |
| 5,278,446 A | 1/1994 | Nagaraj et al. |
| 5,279,029 A | 1/1994 | Burns |
| 5,281,849 A | 1/1994 | Singh Deo et al. |
| 5,285,352 A | 2/1994 | Pastore et al. |
| 5,294,897 A | 3/1994 | Notani et al. |
| 5,327,008 A | 7/1994 | Djennas et al. |
| 5,332,864 A | 7/1994 | Liang et al. |
| 5,335,771 A | 8/1994 | Murphy |
| 5,336,931 A | 8/1994 | Juskey et al. |
| 5,343,076 A | 8/1994 | Katayama et al. |
| 5,358,905 A | 10/1994 | Chiu |
| 5,365,106 A | 11/1994 | Watanabe |
| 5,381,042 A | 1/1995 | Lerner et al. |
| 5,391,439 A | 2/1995 | Tomita et al. |
| 5,406,124 A | 4/1995 | Morita et al. |
| 5,410,180 A | 4/1995 | Fujii et al. |
| 5,414,299 A | 5/1995 | Wang et al. |
| 5,417,905 A | 5/1995 | LeMaire et al. |
| 5,424,576 A | 6/1995 | Djennas et al. |
| 5,428,248 A | 6/1995 | Cha |
| 5,435,057 A | 7/1995 | Bindra et al. |
| 5,444,301 A | 8/1995 | Song et al. |
| 5,452,511 A * | 9/1995 | Chang ............... H01L 23/49537 257/E23.042 |
| 5,454,905 A * | 10/1995 | Fogelson ............... C23F 1/02 216/14 |
| 5,467,032 A | 11/1995 | Lee |
| 5,474,958 A | 12/1995 | Djennas et al. |
| 5,484,274 A | 1/1996 | Neu |
| 5,493,151 A | 2/1996 | Asada et al. |
| 5,508,556 A | 4/1996 | Lin |
| 5,517,056 A * | 5/1996 | Bigler ............... H01L 21/565 257/666 |
| 5,521,429 A | 5/1996 | Aono et al. |
| 5,528,076 A | 6/1996 | Pavio |
| 5,534,467 A | 7/1996 | Rostoker |
| 5,539,251 A | 7/1996 | Iverson et al. |
| 5,543,657 A | 8/1996 | Diffenderfer et al. |
| 5,544,412 A | 8/1996 | Romero et al. |
| 5,545,923 A | 8/1996 | Barber |
| 5,581,122 A | 12/1996 | Chao et al. |
| 5,592,019 A | 1/1997 | Ueda et al. |
| 5,592,025 A | 1/1997 | Clark et al. |
| 5,594,274 A | 1/1997 | Suetaki |
| 5,595,934 A | 1/1997 | Kim |
| 5,604,376 A | 2/1997 | Hamburgen et al. |
| 5,608,265 A | 3/1997 | Kitano et al. |
| 5,608,267 A | 3/1997 | Mahulikar et al. |
| 5,625,222 A | 4/1997 | Yoneda et al. |
| 5,633,528 A | 5/1997 | Abbott et al. |
| 5,637,922 A | 6/1997 | Fillion et al. |
| 5,639,990 A | 6/1997 | Nishihara et al. |
| 5,640,047 A | 6/1997 | Nakashima |
| 5,641,997 A | 6/1997 | Ohta et al. |
| 5,643,433 A | 7/1997 | Fukase et al. |
| 5,644,169 A | 7/1997 | Chun |
| 5,646,831 A | 7/1997 | Manteghi |
| 5,650,663 A | 7/1997 | Parthasarathi |
| 5,661,088 A | 8/1997 | Tessier et al. |
| 5,665,996 A | 9/1997 | Williams et al. |
| 5,673,479 A | 10/1997 | Hawthorne |
| 5,683,806 A | 11/1997 | Sakumoto et al. |
| 5,683,943 A | 11/1997 | Yamada |
| 5,689,135 A | 11/1997 | Ball |
| 5,696,666 A | 12/1997 | Miles et al. |
| 5,701,034 A | 12/1997 | Marrs |
| 5,703,407 A | 12/1997 | Hori |
| 5,710,064 A | 1/1998 | Song et al. |
| 5,723,899 A | 3/1998 | Shin |
| 5,724,233 A | 3/1998 | Honda et al. |
| 5,726,493 A | 3/1998 | Yamashita |
| 5,736,432 A | 4/1998 | Mackessy |
| 5,745,984 A | 5/1998 | Cole, Jr. et al. |
| 5,753,532 A | 5/1998 | Sim |
| 5,753,977 A | 5/1998 | Kusaka et al. |

(56) References Cited

U.S. PATENT DOCUMENTS

| | | | |
|---|---|---|---|
| 5,766,972 A | 6/1998 | Takahashi et al. |
| 5,767,566 A | 6/1998 | Suda |
| 5,770,888 A | 6/1998 | Song et al. |
| 5,776,798 A | 7/1998 | Quan et al. |
| 5,783,861 A | 7/1998 | Son |
| 5,801,440 A | 9/1998 | Chu et al. |
| 5,814,877 A | 9/1998 | Diffenderfer et al. |
| 5,814,881 A | 9/1998 | Alagaratnam et al. |
| 5,814,883 A | 9/1998 | Sawai et al. |
| 5,814,884 A | 9/1998 | Davies et al. |
| 5,817,540 A | 10/1998 | Wark |
| 5,818,105 A | 10/1998 | Kouda |
| 5,821,457 A | 10/1998 | Mosley et al. |
| 5,821,615 A | 10/1998 | Lee |
| 5,834,830 A | 11/1998 | Cho |
| 5,835,988 A | 11/1998 | Ishii |
| 5,844,306 A | 12/1998 | Fujita et al. |
| 5,854,511 A | 12/1998 | Shin et al. |
| 5,854,512 A | 12/1998 | Manteghi |
| 5,856,911 A | 1/1999 | Riley |
| 5,859,471 A | 1/1999 | Kuraishi et al. |
| 5,866,939 A | 2/1999 | Shin et al. |
| 5,866,942 A | 2/1999 | Suzuki et al. |
| 5,871,782 A | 2/1999 | Choi |
| 5,874,784 A | 2/1999 | Aoki et al. |
| 5,877,043 A | 3/1999 | Alcoe et al. |
| 5,886,397 A | 3/1999 | Ewer |
| 5,973,935 A | 10/1999 | Schoenfeld et al. |
| 5,977,630 A | 11/1999 | Woodworth et al. |
| RE36,773 E | 7/2000 | Nomi et al. |
| 6,107,679 A | 8/2000 | Noguchi |
| 6,143,981 A | 11/2000 | Glenn |
| 6,150,709 A * | 11/2000 | Shin ................... H01L 23/3114 257/666 |
| 6,166,430 A | 12/2000 | Yamaguchi |
| 6,169,329 B1 | 1/2001 | Farnworth et al. |
| 6,177,718 B1 | 1/2001 | Kozono |
| 6,181,002 B1 | 1/2001 | Juso et al. |
| 6,184,465 B1 | 2/2001 | Corisis |
| 6,184,573 B1 | 2/2001 | Pu |
| 6,194,777 B1 | 2/2001 | Abbott et al. |
| 6,197,615 B1 | 3/2001 | Song et al. |
| 6,198,171 B1 | 3/2001 | Huang et al. |
| 6,201,186 B1 | 3/2001 | Daniels et al. |
| 6,201,292 B1 | 3/2001 | Yagi et al. |
| 6,204,554 B1 | 3/2001 | Ewer et al. |
| 6,208,020 B1 | 3/2001 | Minamio et al. |
| 6,208,021 B1 | 3/2001 | Ohuchi et al. |
| 6,208,023 B1 | 3/2001 | Nakayama et al. |
| 6,211,462 B1 | 4/2001 | Carter, Jr. et al. |
| 6,218,731 B1 | 4/2001 | Huang et al. |
| 6,222,258 B1 | 4/2001 | Asano et al. |
| 6,222,259 B1 | 4/2001 | Park et al. |
| 6,225,146 B1 | 5/2001 | Yamaguchi et al. |
| 6,229,200 B1 | 5/2001 | McClellan et al. |
| 6,229,205 B1 | 5/2001 | Jeong et al. |
| 6,238,952 B1 | 5/2001 | Lin et al. |
| 6,239,367 B1 | 5/2001 | Hsuan et al. |
| 6,239,384 B1 | 5/2001 | Smith et al. |
| 6,242,281 B1 | 6/2001 | McClellan et al. |
| 6,250,774 B1 * | 6/2001 | Begemann ............... F21S 8/086 362/231 |
| 6,256,200 B1 | 7/2001 | Lam et al. |
| 6,258,629 B1 | 7/2001 | Niones et al. |
| 6,261,864 B1 | 7/2001 | Jung et al. |
| 6,281,566 B1 | 8/2001 | Magni |
| 6,281,568 B1 | 8/2001 | Glenn et al. |
| 6,282,094 B1 | 8/2001 | Lo et al. |
| 6,282,095 B1 | 8/2001 | Houghton et al. |
| 6,285,075 B1 | 9/2001 | Combs et al. |
| 6,291,271 B1 | 9/2001 | Lee et al. |
| 6,291,273 B1 | 9/2001 | Miyaki et al. |
| 6,294,100 B1 | 9/2001 | Fan et al. |
| 6,294,830 B1 | 9/2001 | Fjelstad |
| 6,295,977 B1 | 10/2001 | Ripper et al. |
| 6,297,548 B1 | 10/2001 | Moden et al. |
| 6,303,984 B1 | 10/2001 | Corisis |
| 6,303,997 B1 | 10/2001 | Lee |
| 6,306,685 B1 | 10/2001 | Liu et al. |
| 6,307,272 B1 | 10/2001 | Takahashi et al. |
| 6,309,909 B1 | 10/2001 | Ohgiyama |
| 6,316,822 B1 | 11/2001 | Vekateshwaran et al. |
| 6,316,838 B1 | 11/2001 | Ozawa et al. |
| 6,323,550 B1 | 11/2001 | Martin et al. |
| 6,326,243 B1 | 12/2001 | Suzuya et al. |
| 6,326,244 B1 | 12/2001 | Brooks et al. |
| 6,326,678 B1 | 12/2001 | Karmezos et al. |
| 6,335,564 B1 | 1/2002 | Pour |
| 6,337,510 B1 | 1/2002 | Chun-Jen et al. |
| 6,338,984 B2 | 1/2002 | Minamio et al. |
| 6,339,252 B1 | 1/2002 | Niones et al. |
| 6,339,255 B1 | 1/2002 | Shin |
| 6,342,730 B1 | 1/2002 | Jung et al. |
| 6,348,726 B1 * | 2/2002 | Bayan ................. H01L 23/3107 257/666 |
| 6,355,502 B1 | 3/2002 | Kang et al. |
| 6,359,221 B1 | 3/2002 | Yamada et al. |
| 6,362,525 B1 | 3/2002 | Rahim |
| 6,369,447 B2 | 4/2002 | Mori |
| 6,369,454 B1 | 4/2002 | Chung |
| 6,373,127 B1 | 4/2002 | Baudouin et al. |
| 6,377,464 B1 | 4/2002 | Hashemi et al. |
| 6,380,048 B1 | 4/2002 | Boon et al. |
| 6,384,472 B1 | 5/2002 | Huang |
| 6,388,336 B1 | 5/2002 | Venkateshwaran et al. |
| 6,395,578 B1 | 5/2002 | Shin et al. |
| 6,399,415 B1 | 6/2002 | Bayan et al. |
| 6,400,004 B1 | 6/2002 | Fan et al. |
| 6,410,979 B2 | 6/2002 | Abe |
| 6,414,385 B1 | 7/2002 | Huang et al. |
| 6,420,779 B1 | 7/2002 | Sharma et al. |
| 6,421,013 B1 | 7/2002 | Chung |
| 6,423,643 B1 | 7/2002 | Furuhata et al. |
| 6,429,508 B1 | 8/2002 | Gang |
| 6,437,429 B1 | 8/2002 | Su et al. |
| 6,444,499 B1 | 9/2002 | Swiss et al. |
| 6,448,633 B1 | 9/2002 | Yee et al. |
| 6,452,279 B2 | 9/2002 | Shimoda |
| 6,459,148 B1 | 10/2002 | Chun-Jen et al. |
| 6,464,121 B2 | 10/2002 | Reijnders |
| 6,465,883 B2 | 10/2002 | Olofsson |
| 6,472,735 B2 | 10/2002 | Isaak |
| 6,475,646 B2 | 11/2002 | Park et al. |
| 6,476,469 B2 | 11/2002 | Huang et al. |
| 6,476,474 B1 | 11/2002 | Hung |
| 6,482,680 B1 | 11/2002 | Khor et al. |
| 6,483,178 B1 | 11/2002 | Chuang |
| 6,492,718 B2 | 12/2002 | Ohmori et al. |
| 6,495,909 B2 | 12/2002 | Jung et al. |
| 6,498,099 B1 | 12/2002 | MClellan et al. |
| 6,498,392 B2 | 12/2002 | Azuma |
| 6,507,096 B2 | 1/2003 | Gang |
| 6,507,120 B2 | 1/2003 | Lo et al. |
| 6,518,089 B2 | 2/2003 | Coyle |
| 6,525,942 B2 | 2/2003 | Huang et al. |
| 6,528,893 B2 | 3/2003 | Jung et al. |
| 6,534,849 B1 | 3/2003 | Gang |
| 6,545,332 B2 | 4/2003 | Huang |
| 6,545,345 B1 | 4/2003 | Glenn et al. |
| 6,552,421 B2 | 4/2003 | Kishimoto et al. |
| 6,559,525 B2 | 5/2003 | Huang |
| 6,566,168 B2 | 5/2003 | Gang |
| 6,580,161 B2 | 6/2003 | Kobayakawa |
| 6,583,503 B2 | 6/2003 | Akram et al. |
| 6,585,905 B1 | 7/2003 | Fan et al. |
| 6,603,196 B2 | 8/2003 | Lee et al. |
| 6,624,005 B1 | 9/2003 | DiCaprio et al. |
| 6,627,977 B1 | 9/2003 | Foster |
| 6,646,339 B1 | 11/2003 | Ku |
| 6,667,546 B2 | 12/2003 | Huang et al. |
| 6,677,663 B1 | 1/2004 | Ku et al. |
| 6,686,649 B1 | 2/2004 | Matthews et al. |
| 6,696,752 B2 | 2/2004 | Su et al. |
| 6,700,189 B2 | 3/2004 | Shibata |

(56) References Cited

U.S. PATENT DOCUMENTS

| | | | |
|---|---|---|---|
| 6,713,375 B2 | 3/2004 | Shenoy | |
| 6,757,178 B2 | 6/2004 | Okabe et al. | |
| 6,800,936 B2 | 10/2004 | Kosemura et al. | |
| 6,812,552 B2 | 11/2004 | Islam et al. | |
| 6,818,973 B1 | 11/2004 | Foster | |
| 6,858,919 B2 | 2/2005 | Seo et al. | |
| 6,861,734 B2* | 3/2005 | Minamio | H01L 21/4842 257/666 |
| 6,867,492 B2 | 3/2005 | Auburger et al. | |
| 6,876,068 B1 | 4/2005 | Lee et al. | |
| 6,878,571 B2 | 4/2005 | Isaak et al. | |
| 6,897,552 B2 | 5/2005 | Nakao | |
| 6,927,478 B2 | 8/2005 | Paek | |
| 6,967,125 B2 | 11/2005 | Fee et al. | |
| 6,995,459 B2 | 2/2006 | Lee et al. | |
| 7,002,805 B2 | 2/2006 | Lee et al. | |
| 7,005,327 B2 | 2/2006 | Kung et al. | |
| 7,015,571 B2 | 3/2006 | Chang et al. | |
| 7,045,396 B2 | 5/2006 | Crowley et al. | |
| 7,053,469 B2 | 5/2006 | Koh et al. | |
| 7,075,816 B2 | 7/2006 | Fee et al. | |
| 7,102,209 B1 | 9/2006 | Bayan et al. | |
| 7,109,572 B2 | 9/2006 | Fee et al. | |
| 7,185,426 B1 | 3/2007 | Hiner et al. | |
| 7,193,298 B2* | 3/2007 | Hong | H01L 23/49541 257/666 |
| 7,211,471 B1 | 5/2007 | Foster | |
| 7,242,081 B1 | 7/2007 | Lee | |
| 7,245,007 B1 | 7/2007 | Foster | |
| 7,253,503 B1 | 8/2007 | Fusaro et al. | |
| 7,311,423 B2* | 12/2007 | Frecska | F21S 8/04 362/150 |
| 7,808,084 B1* | 10/2010 | Lee | H01L 23/49503 257/666 |
| 7,928,542 B2* | 4/2011 | Lee | H01L 23/3107 257/666 |
| 7,986,032 B2* | 7/2011 | Chow | H01L 23/3107 257/666 |
| 7,997,770 B1* | 8/2011 | Meurer | F21K 9/27 362/171 |
| 8,029,159 B2* | 10/2011 | Chen | F21S 6/003 362/231 |
| 8,184,453 B1* | 5/2012 | Kim | H01L 21/4828 361/768 |
| 8,188,579 B1* | 5/2012 | Kim | H01L 23/49503 257/666 |
| 8,330,362 B2* | 12/2012 | Lin | F21V 3/02 313/512 |
| 8,360,599 B2* | 1/2013 | Ivey | F21V 23/06 362/218 |
| 8,901,823 B2* | 12/2014 | Scapa | F21V 23/0457 315/131 |
| 2001/0008305 A1 | 7/2001 | McClellan et al. | |
| 2001/0014538 A1 | 8/2001 | Kwan et al. | |
| 2002/0011654 A1 | 1/2002 | Kimura | |
| 2002/0024122 A1 | 2/2002 | Jung et al. | |
| 2002/0027297 A1 | 3/2002 | Ikenaga et al. | |
| 2002/0038873 A1 | 4/2002 | Hiyoshi | |
| 2002/0060526 A1* | 5/2002 | Timmermans | H05B 33/0803 315/246 |
| 2002/0072147 A1 | 6/2002 | Sayanagi et al. | |
| 2002/0111009 A1 | 8/2002 | Huang et al. | |
| 2002/0140061 A1 | 10/2002 | Lee | |
| 2002/0140068 A1 | 10/2002 | Lee et al. | |
| 2002/0140081 A1 | 10/2002 | Chou et al. | |
| 2002/0158318 A1 | 10/2002 | Chen | |
| 2002/0163015 A1 | 11/2002 | Lee et al. | |
| 2002/0167060 A1 | 11/2002 | Buijsman et al. | |
| 2003/0006055 A1 | 1/2003 | Chien-Hung et al. | |
| 2003/0030131 A1 | 2/2003 | Lee et al. | |
| 2003/0059644 A1 | 3/2003 | Datta et al. | |
| 2003/0064548 A1 | 4/2003 | Isaak | |
| 2003/0073265 A1 | 4/2003 | Hu et al. | |
| 2003/0102537 A1 | 6/2003 | McLellan et al. | |
| 2003/0164554 A1 | 9/2003 | Fee et al. | |
| 2003/0168719 A1* | 9/2003 | Cheng | H01L 23/3107 257/666 |
| 2003/0198032 A1 | 10/2003 | Collander et al. | |
| 2004/0027788 A1 | 2/2004 | Chiu et al. | |
| 2004/0056277 A1 | 3/2004 | Karnezos | |
| 2004/0061212 A1 | 4/2004 | Karnezos | |
| 2004/0061213 A1 | 4/2004 | Karnezos | |
| 2004/0063242 A1 | 4/2004 | Karnezos | |
| 2004/0063246 A1 | 4/2004 | Karnezos | |
| 2004/0065963 A1 | 4/2004 | Karnezos | |
| 2004/0080025 A1 | 4/2004 | Kasahara et al. | |
| 2004/0089926 A1 | 5/2004 | Hsu et al. | |
| 2004/0164387 A1 | 8/2004 | Ikenaga et al. | |
| 2004/0253803 A1 | 12/2004 | Tomono et al. | |
| 2006/0087020 A1 | 4/2006 | Hirano et al. | |
| 2006/0157843 A1 | 7/2006 | Hwang | |
| 2006/0216868 A1 | 9/2006 | Yang et al. | |
| 2006/0231939 A1 | 10/2006 | Kawabata et al. | |
| 2007/0023202 A1 | 2/2007 | Shibata | |
| 2008/0062689 A1* | 3/2008 | Villard | F21V 14/02 362/249.07 |
| 2008/0094837 A1* | 4/2008 | Dobbins | F21K 9/00 362/249.01 |
| 2008/0122048 A1* | 5/2008 | Chan | H01L 21/4842 257/666 |
| 2008/0230887 A1 | 9/2008 | Sun et al. | |
| 2008/0283862 A1* | 11/2008 | Fujii | H01L 33/486 257/99 |
| 2008/0283980 A1* | 11/2008 | Gao | H01L 23/49541 257/670 |
| 2009/0323330 A1* | 12/2009 | Gordin | F21V 5/04 362/235 |
| 2011/0049685 A1* | 3/2011 | Park | H01L 23/3107 257/660 |
| 2011/0108963 A1* | 5/2011 | Balakrishnan | H01L 23/3107 257/670 |
| 2011/0227205 A1* | 9/2011 | Lu | H01L 23/49537 257/670 |
| 2012/0049203 A1* | 3/2012 | Mondada | H01L 25/0753 257/88 |
| 2012/0126260 A1* | 5/2012 | Hussell | F21V 3/00 257/88 |
| 2013/0258668 A1* | 10/2013 | Dellian | F21V 17/08 362/249.02 |
| 2014/0151731 A1* | 6/2014 | Tran | H01L 33/50 257/98 |

FOREIGN PATENT DOCUMENTS

| | | |
|---|---|---|
| EP | 0459493 | 12/1991 |
| EP | 0720234 | 3/1996 |
| EP | 07020225 | 3/1996 |
| EP | 0794572 A2 | 10/1997 |
| EP | 0844665 | 5/1998 |
| EP | 0989608 | 3/2000 |
| EP | 1032037 | 8/2000 |
| JP | 55163868 | 12/1980 |
| JP | 5745959 | 3/1982 |
| JP | 58160096 | 8/1983 |
| JP | 59208756 | 11/1984 |
| JP | 59227143 | 12/1984 |
| JP | 60010756 | 1/1985 |
| JP | 60116239 | 8/1985 |
| JP | 60195957 | 10/1985 |
| JP | 60231349 | 11/1985 |
| JP | 6139555 | 2/1986 |
| JP | 61248541 | 11/1986 |
| JP | 629639 | 1/1987 |
| JP | 6333854 | 2/1988 |
| JP | 63067762 | 3/1988 |
| JP | 63188964 | 8/1988 |
| JP | 63205935 | 8/1988 |
| JP | 63233555 | 9/1988 |
| JP | 62349345 | 10/1988 |
| JP | 63289951 | 11/1988 |
| JP | 63316470 | 12/1988 |
| JP | 64054749 | 3/1989 |

(56) References Cited

FOREIGN PATENT DOCUMENTS

| | | |
|---|---|---|
| JP | 1106456 | 4/1989 |
| JP | 1175250 | 7/1989 |
| JP | 1205544 | 8/1989 |
| JP | 1251747 | 10/1989 |
| JP | 2129948 | 5/1990 |
| JP | 369248 | 7/1991 |
| JP | 3177060 | 8/1991 |
| JP | 3289162 | 12/1991 |
| JP | 4098864 | 3/1992 |
| JP | 5129473 | 5/1993 |
| JP | 5166992 | 7/1993 |
| JP | 5283460 | 10/1993 |
| JP | 6061401 | 3/1994 |
| JP | 692076 | 4/1994 |
| JP | 6140563 | 5/1994 |
| JP | 652333 | 9/1994 |
| JP | 6252333 | 9/1994 |
| JP | 6260532 | 9/1994 |
| JP | 7297344 | 11/1995 |
| JP | 7312405 | 11/1995 |
| JP | 8064364 | 3/1996 |
| JP | 8083877 | 3/1996 |
| JP | 8125066 | 5/1996 |
| JP | 964284 | 6/1996 |
| JP | 8222682 | 8/1996 |
| JP | 8306853 | 11/1996 |
| JP | 98205 | 1/1997 |
| JP | 98206 | 1/1997 |
| JP | 98207 | 1/1997 |
| JP | 992775 | 4/1997 |
| JP | 9260568 | 10/1997 |
| JP | 9293822 | 11/1997 |
| JP | 10022447 | 1/1998 |
| JP | 10199934 | 7/1998 |
| JP | 10256240 | 9/1998 |
| JP | 11307675 | 11/1999 |
| JP | 2000150765 | 5/2000 |
| JP | EP 1032037 A2 * | 8/2000 ........... H01L 21/565 |
| JP | 20010600648 | 3/2001 |
| JP | 2002519848 | 7/2002 |
| JP | 200203497 | 8/2002 |
| JP | 2003243595 | 8/2003 |
| JP | 2004158753 | 6/2004 |
| KR | 941979 | 1/1994 |
| KR | 19940010938 | 5/1994 |
| KR | 19950018924 | 6/1995 |
| KR | 19950041844 | 11/1995 |
| KR | 19950044554 | 11/1995 |
| KR | 19950052621 | 12/1995 |
| KR | 1996074111 | 12/1996 |
| KR | 9772358 | 11/1997 |
| KR | 100220154 | 6/1999 |
| KR | 20000072714 | 12/2000 |
| KR | 20000086238 | 12/2000 |
| KR | 20020049944 | 6/2002 |
| WO | 2009036671 | 8/1999 |
| WO | 9956316 | 11/1999 |
| WO | 9967821 | 12/1999 |

OTHER PUBLICATIONS

Vishay, "4 Milliohms in the So-8: Vishay Siliconix Sets New Record for Power MOSFET On-Resistance," Press Release from webpage, 3 pages, www.vishay.com/news/releases, Nov. 7, 2002.
Patrick Mannion, "MOSFETs Break out of the Shackles of Wire Bonding," Informational Packet, 5 pages, Electronic No. 6, www.elecdesign.com/1999/mar2299/ti/0322ti1.shtml.

* cited by examiner

SEMICONDUCTOR DEVICE INCLUDING LEADFRAME WITH A COMBINATION OF LEADS AND LANDS AND METHOD

CROSS-REFERENCE TO RELATED APPLICATIONS

The present application is a continuation of U.S. application Ser. No. 14/983,938 filed Dec. 30, 2015 and issued as U.S. Pat. No. 9,508,631 on Nov. 29, 2016, which is a continuation of U.S. application Ser. No. 14/106,139 filed Dec. 13, 2013 and issued as U.S. Pat. No. 9,275,939 on Mar. 1, 2016, which is a continuation application of U.S. application Ser. No. 13/015,071 filed Jan. 27, 2011 and issued as U.S. Pat. No. 8,648,450 B1 on Feb. 11, 2014, all of which are incorporated herein by reference in their entirety to provide continuity of disclosure.

STATEMENT RE: FEDERALLY SPONSORED RESEARCH/DEVELOPMENT

Not Applicable

BACKGROUND

1. Field of the Invention

The present invention relates generally to integrated circuit package technology and, more particularly, to an increased capacity semiconductor device or package which includes a combination of leads and lands, with the lands being provided in a prescribed arrangement and exposed within a common exterior surface of the package body of the device.

2. Description of the Related Art

Semiconductor dies are conventionally enclosed in plastic packages that provide protection from hostile environments and enable electrical interconnection between the semiconductor die and an underlying substrate such as a printed circuit board (PCB) or motherboard. The elements of such a package include a metal leadframe, an integrated circuit or semiconductor die, bonding material to attach the semiconductor die to the leadframe, bond wires which electrically connect pads on the semiconductor die to individual leads of the leadframe, and a hard plastic encapsulant material which covers the other components and forms the exterior of the semiconductor package commonly referred to as the package body.

The leadframe is the central supporting structure of such a package, and is typically fabricated by chemically etching or mechanically stamping a metal strip. A portion of the leadframe is internal to the package, i.e., completely surrounded by the plastic encapsulant or package body. Portions of the leads of the leadframe may extend externally from the package body or may be partially exposed therein for use in electrically connecting the package to another component. In certain semiconductor packages, a portion of the die pad of the leadframe also remains exposed within the package body.

Leadframes for semiconductor devices or packages can be largely classified into copper-based leadframes (copper/iron/phosphorous; 99.8/0.01/0.025), copper alloy-based leadframes (copper/chromium/tin/zinc; 99.0/0.25/0.22), and alloy 42-based leadframes (iron/nickel; 58.0/42.0) according to the composition of the elements or materials included in the leadframe. Exemplary semiconductor devices employing leadframes include a through-hole mounting dual type inline package (DIP), a surface mounting type quad flat package (QFP), and a small outline package (SOP). In recent years, land grid array type semiconductor devices using leadframes have also been developed for use in certain applications.

The aforementioned semiconductor devices are particularly advantageous for their smaller size and superior electrical performance. In the electronics industry and, in particular, in high frequency applications such hard disk drives, digital television and other consumer electronics, there is an increasing need for exposed pad semiconductor devices of increased functional capacity, coupled with reduced size and weight. In view of this need, conventional leadframe structures as currently known and integrated into existing semiconductor devices often prove to be unsatisfactory. The present invention provides a semiconductor device which addresses the aforementioned needs by providing increased I/O with a reduced overall size. The semiconductor device of the present invention includes a leadframe having a combination of leads and lands, with the lands being provided in a prescribed arrangement and exposed within a common exterior surface of the package body of the device. The leadframe of the semiconductor device may be fabricated in accordance with standard, low-cost forming techniques, with sawing, punching, etching, or other material removal processes may be completed during the fabrication of the semiconductor device to effectively electrically isolate various leads from each other within the semiconductor device. These, as well as other features and attributes of the present invention will be discussed in more detail below.

BRIEF DESCRIPTION OF THE DRAWINGS

These, as well as other features of the present invention, will become more apparent upon reference to the drawings wherein.

Common reference numerals are used throughout the drawings and detailed description to indicate like elements.

DETAILED DESCRIPTION OF THE INVENTION DRAWINGS

Figure 7A:
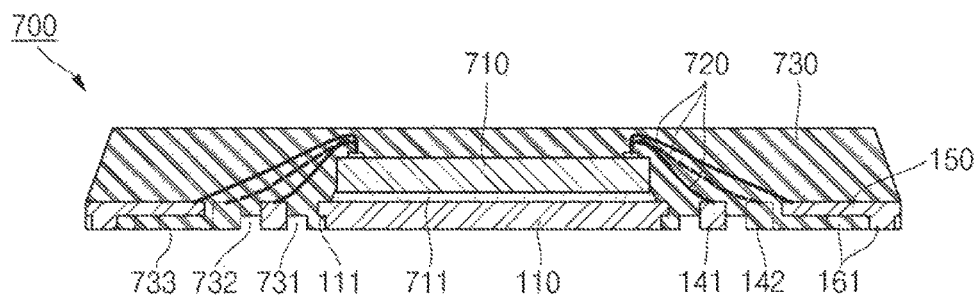
FIG. 7A is a cross-sectional view of the semiconductor device of the first embodiment as fabricated to include the leadframe shown in FIGS. 1A and 1B.
Figure 7B:
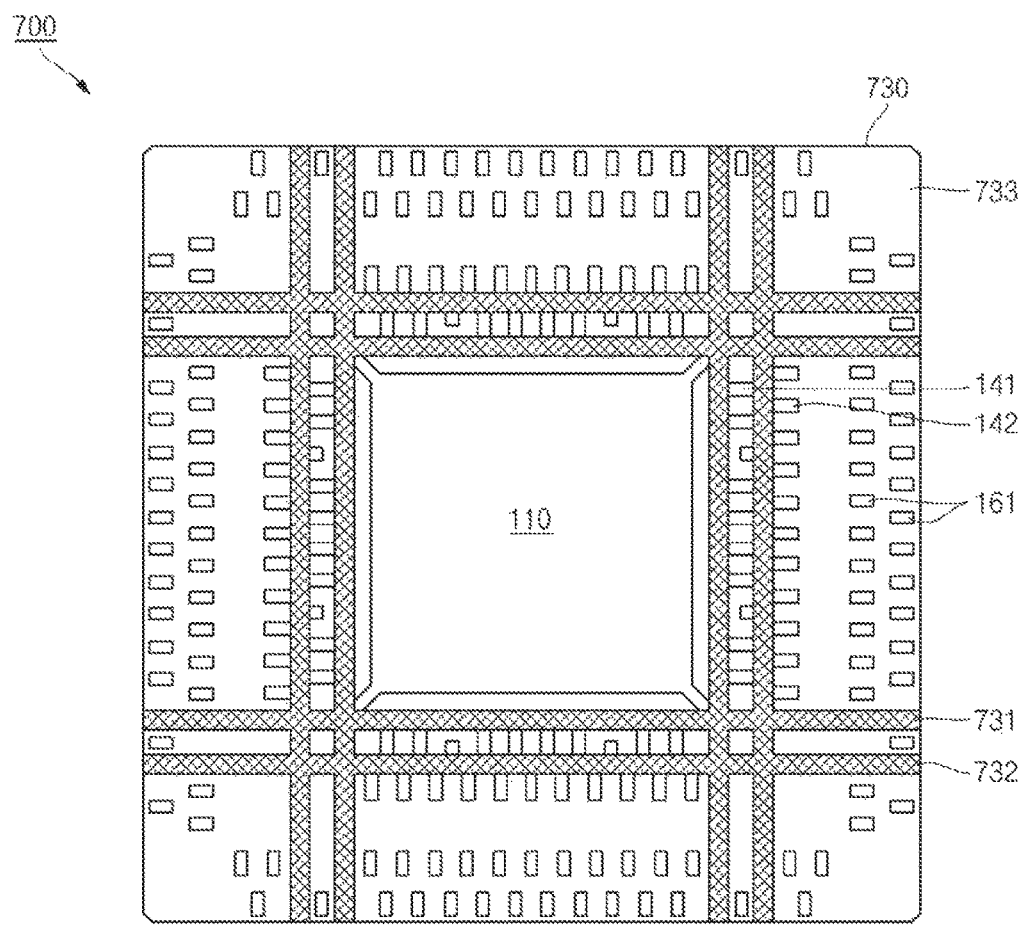
FIG. 7B is a bottom plan view of the semiconductor device of the first embodiment shown in FIG. 7A.

Referring now to the drawings wherein the showings are for purposes of illustrating preferred embodiments of the present invention only, and not for purposes of limiting the same, FIGS. 7A and 7B depict a semiconductor package or device 700 constructed in accordance with a first embodiment of the present invention. The leadframe 100 integrated into the semiconductor package 200 is shown in its unsingulated state in FIGS. 1A and 1B.

Figure 1A:
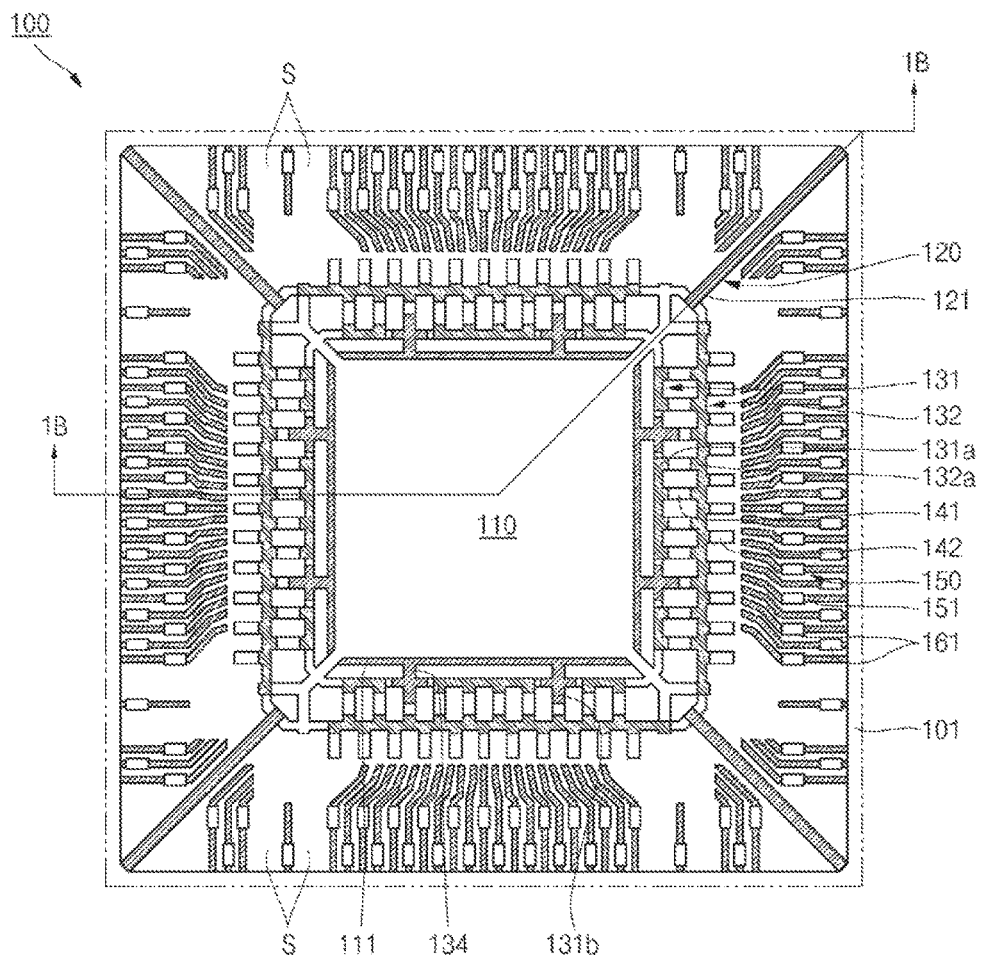
FIG. 1A is a top plan view of an unsingulated leadframe which is integrated into a semiconductor device or package constructed in accordance with a first embodiment of the present invention.
Figure 1B:
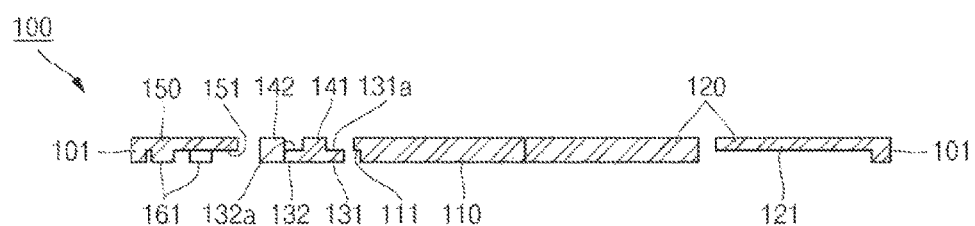
FIG. 1B is a cross-sectional view of the leadframe taken along line 1B-1B of FIG. 1A.

Referring now to FIGS. 1A and 1B, the leadframe 100 comprises a generally quadrangular (e.g., square) die paddle or die pad 110 which defines four peripheral edge segments. Additionally, when viewed from the perspective shown in FIG. 1B, the die pad 110 defines opposed, generally planar top and bottom surfaces. As seen in FIGS. 1A and 1B, the die pad 110 of the leadframe 100 is not of uniform thickness. Rather, a peripheral portion of the bottom surface of the die pad 110 is partially etched (e.g., half-etched) to define an etched surface 111. More particularly, the etched surface 111, which is recessed relative to the remainder of the bottom surface of the die pad 110, is segregated into four segments, with each of these segments extending along a respective one of peripheral edge segments of the die pad 110 and between a respective pair of tie bars 120 of the leadframe 100 which are described in more detail below. In FIG. 1A, which is a bottom plan view of the leadframe 100, the etched surface 111 in the bottom surface of the die pad 110 is indicated by the condensed hatching which slopes downwardly from right to left.

As will be discussed in more detail below, in the fabrication process for the semiconductor device 700 including the leadframe 100, a semiconductor die is attached to the top surface of the die pad 110 through the use of an adhesive layer, with an encapsulant material thereafter being applied to the semiconductor die and the leadframe 100 to form the package body of the semiconductor device 700. Advantageously, the etched surface 111 formed in the peripheral portion of the bottom surface of the die pad 110 as indicated above effectively increases the distance along which moisture must travel to reach the semiconductor die mounted to the top surface of the die pad 110. As a result, such semiconductor die is safely protected against moisture in the completed semiconductor device 700. Additionally, the flow of encapsulant material over the etched surface 111 during the formation of the package body of the semiconductor device 700 facilitates the creation of a mechanical interlock between the package body and the die pad 110.

As indicated above, integrally connected to the die pad 110 are a plurality of tie bars 120. More particularly, the leadframe 100 includes four tie bars 120 which extend diagonally from respective ones of the four corner regions defined by the die pad 110. As seen in FIG. 1A, the tie bars 120 are integrally connected to a generally quadrangular frame or dambar 101 which circumvents the die pad 110 and is disposed in spaced relation thereto. The tie bars 120 are identically configured to each other, and extend diagonally outwardly at predetermined lengths from respective ones of the corner regions of the die pad 110, with the integral connection of the tie bars 120 to the dambar 101 effectively supporting the die pad 110 within the interior of the dambar 101. However, as is apparent from FIG. 1A, each of the tie bars 120 does not have an uninterrupted, linear configuration. Rather, each of the tie bars 120 defines inner and outer generally straight or linear portions which are separated from each other by a generally triangular portion, the inner linear portion being integrally connected to and extending from a respective corner region of the die pad 110, and the outer linear portion extending and being integrally connected to the dambar 101. As seen in FIG. 1B, the triangular portion included in each dambar 120 effectively creates a gap or space separating the adjacent ends of the inner and outer linear portions thereof from each other.

When viewed from the perspective shown in FIG. 1B, each of the tie bars 120 defines opposed, generally planar top and bottom surfaces which extend in generally co-planar relation to respective ones of the top and bottom surface of the die pad 110. However, a portion of the bottom surface of each tie bar 120 is preferably partially etched (e.g., half-etched) to define an etched surface 121. As seen in FIGS. 1A and 1B, the etched surface 121 of each tie bar 120, which is recessed relative to the remainder of the bottom surface of the tie bar 120, extends along the entire length of the outer linear portion thereof. As such, one end of the etched surface 121 of each tie bar 120 terminates at the dambar 101, with the opposite end terminating at the aforementioned gap separating the inner and outer linear portions of each tie bar 120 from each other. The etched surface 121 of each tie bar 120 extends in generally co-planar relation to the etched surface 111 of the die pad 110. In FIG. 1A, the etched surface 121 in the bottom surface of each tie bar 120 is indicated by the condensed hatching which slopes downwardly from right to left. During the fabrication process for the semiconductor device 700 including the leadframe 100, the encapsulant material used to form the package body of the semiconductor device 700 is also able to flow over the etched surfaces 121 of the tie bars 120, thus resulting in the outer linear portions of the tie bars 120 being encapsulated by the package body of the semiconductor device 700 which enhances the bonding or mechanical interlock therebetween.

As indicated above, the tie bars 120 are integrally connected to the dambar 101 which circumvents the die pad 110. In the leadframe 100, the dambar 101 is provided in the form of a substantially quadrangular (e.g., square) ring which interconnects the distal ends of the tie bars 120. As best seen in FIG. 1A, the dambar 101 defines four peripheral segments which extend in spaced, generally parallel relation to respective ones of the peripheral edge segments of the die pad 110. In a fabrication process for the semiconductor package 700 which will be described in more detail below, the dambar 101 is singulated or removed from the leadframe 100 to electrically isolate other structural features of the leadframe 100 from each other.

The leadframe 100 further comprises a first (inner) support bar 131 and a second (outer) support bar 132 which are each integrally connected to the tie bars 120 and circumvent the die pad 110, with the second support bar 132 further circumventing the first support bar 131 which is positioned between the die pad 110 and second support bar 132 as described in more detail below. More particularly, as seen in FIG. 1A, the first support bar 131 has a generally quadrangular (e.g., square) configuration and defines four peripheral segments which extend in spaced, generally parallel relation to respective ones of the peripheral edge segments of the die pad 110. Similarly, the second support bar 132 also has a generally quadrangular (e.g., square) configuration, and includes four peripheral segments which extend in spaced, generally parallel relation to respective ones of the peripheral edge segments of the die pad 110. Thus, the first and second support bars 131, 132 are concentrically positioned between the die pad 110 and the dambar 101, with the first support bar 131 being concentrically positioned between the die pad 110 and the second support bar 132. Each peripheral segment of the first support bar 131 is integrally connected to and extends between a corresponding adjacent pair of the tie bars 120, as does each peripheral segment of the second support bar 132.

As further seen in FIG. 1A, in addition to being integrally connected to the tie bars 120, the first support bar 131 is also integrally connected to the die pad 110. More particularly, the leadframe 100 preferably includes a plurality of auxiliary tie bars 134 which are integrally connected to and extend between the die pad 110 and the first support bar 131. In this regard, the auxiliary tie bars 134 function to connect the die pad 110 to and to support the die pad 110 within the interior of the first support bar 131. In the leadframe 100, a total of eight auxiliary tie bars 134 are included therein, and segregated into four sets of two auxiliary tie bars 134 each. In this regard, each set of two auxiliary tie bars 134 is integrally connected to and extends generally perpendicularly between a respective one of the peripheral segments of the first support bar 131 and the adjacent, corresponding peripheral edge segment of the die pad 110. In the leadframe 100, each of the auxiliary tie bars 134 is subjected to a partial etching process (e.g., is half-etched) so as to define a generally planar top surface which extends in generally co-planar relation to the top surface of the die pad 110, and an opposed, etched surface which defines the bottom surface thereof. In FIG. 1A, the etched bottom surface of each auxiliary tie bar 134 is indicated by the condensed hatching which slopes downwardly from right to left. As further evident from FIG. 1A, the etched bottom surfaces of the auxiliary tie bars 134 are substantially flush or co-planar with the etched surface 111 of the die pad 110. As such, during the formation of the package body of the semiconductor device 700, the encapsulant material used to form the package body will also flow over the etched bottom surfaces of the auxiliary tie bars 134 and thus completely cover or encapsulate the same. Such encapsulation of the auxiliary tie bars 134 prevents the same from affecting the connection of the completed semiconductor device 700 to an external circuit. Those of ordinary skill in the art will recognize that the inclusion of eight auxiliary tie bars 134 in the leadframe 100 in the aforementioned arrangement is exemplary only, and may be modified without departing from the spirit and scope of the present invention.

In the leadframe 100, the first and second support bars 131, 132 each define opposed, generally planar top and bottom surfaces which extends in generally co-planar relation to respective ones of the top and bottom surfaces of the die pad 110. However, as seen in FIGS. 1A and 1B, the first and second support bars 131, 132 are not of uniform thickness. Rather, a portion of the top surface of the first support bar 131 within each of the four peripheral segments thereof is partially etched (e.g., half-etched) to define an etched surface 131a. Similarly, a portion of the top surface of the second support bar 132 within each of the four peripheral segments thereof is partially etched (e.g., half-etched) to define an etched surface 132a. Thus, the etched surfaces 131a, 132a, which are recessed relative to the top surfaces of respective ones of the first and second support bars 131, 132, are each segregated into four segments which extend within respective ones of the four peripheral segments of corresponding ones of the first and second support bars 131, 132. In FIG. 1A, which is a bottom plan view of the leadframe 100 as indicated above, the etched surfaces 131a, 132a are indicated by the condensed hatching which slopes downwardly from left to right (rather than from right to left). In the leadframe 100, the etched surfaces 131a, 132a preferably extend in generally coplanar relation to the etched surface 111 of the die pad 110.

As further seen in FIG. 1A, in the leadframe 100, a portion of the bottom surface of the first support bar 131 within each of the four peripheral segments thereof is partially etched (e.g., half-etched) to define an etched surface 131b. More particularly, the etched surface 131b, which is recessed relative to the bottom surface of the first support bar 131, is preferably segregated into eight sections, two of which are formed in each of the four peripheral segments first support bar 131 in alignment with respective one of the auxiliary tie bars 134 of the corresponding set thereof. In FIG. 1A, which is a bottom plan view of the leadframe 100 as indicated above, the etched surfaces 131b are indicated by the condensed hatching which slopes downwardly from right to left (rather than from left to right). In the leadframe 100, the etched surfaces 131b also preferably extend in generally coplanar relation to the etched surface 111 of the die pad 110. In a fabrication process for the semiconductor package 700 which will be described in more detail below, the first and second support bars 131, 132 are singulated or removed from the leadframe 100 to electrically isolate other structural features of the leadframe 100 from each other.

The leadframe 100 further comprises a plurality of first (inner) lands 141 which are each integrally connected to and extend between the first and second support bars 131, 132. More particularly, as best seen in FIG. 1A, the first lands 141 are segregated into four sets, with each set of the first lands 141 being integrally connected to and extending generally perpendicularly between a corresponding pair of the peripheral segments defined by the first and second support bars 131, 132. As seen in FIG. 1B, each of the first lands 141 defines opposed, generally planar top and bottom surfaces which extend in generally co-planar relation to respective ones of the top and bottom surfaces of the die pad 110. The first lands 141 of each set thereof are also preferably arranged at a predetermined pitch.

The leadframe 100 further comprises a plurality of second (outer) lands 142 which are integrally connected to the second support bar 132 and extend outwardly toward the dambar 101. More particularly, the second lands 142 are also segregated into four sets, with the second lands 142 of each set being integrally connected to and extending generally perpendicularly outward from a respective one of the four peripheral segments defined by the second support bar 132. The second lands 142 of each set are arranged at a predetermined pitch and protrude perpendicularly outward at a predetermined length from a respective one of the peripheral segments of the second support bar 132. Additionally, as seen in FIG. 1A, the second lands 142 of each set thereof are preferably staggered or offset relative to that set of the first lands 141 integrally connected to the same peripheral segment of the second support bar 132. Like the first lands 141, the second lands 142 each define opposed, generally planar top and bottom surfaces which preferably extend in generally co-planar relation to respective ones of the top and bottom surfaces of the die pad 110.

The leadframe 100 constructed in accordance with the present invention further comprises a plurality of leads 150 which are integrally connected to the dambar 101 and extend inwardly toward the die pad 110 in spaced relation thereto. More particularly, the leads 150, like the first and second lands 141, 142, are preferably segregated into four sets, with each set of the leads 150 extending between an adjacent pair of the tie bars 120. The leads 150 of each set also extend toward a corresponding peripheral edge segment of the die pad 110, and are arranged at a predetermined pitch. As further seen in FIG. 1A, two of the leads 150 of each set have a generally linear configuration, and extend generally perpendicularly from a corresponding peripheral segment of the dambar 101. However, the remaining leads 150 of each set each preferably have an angled configuration so as to extend toward a respective one of the peripheral edge segments of the die pad 110.

When viewed from the perspective shown in FIG. 1B, each of the leads 150 defines opposed, generally planar top and bottom surfaces which extend in generally co-planar relation to respective ones of the top and bottom surfaces of the die pad 110. However, a portion of the bottom surface of each lead 150 is preferably partially etched (e.g., half-etched) to define an etched surface 151. As seen in FIGS. 1A and 1B, the etched surface 151 of each lead 150, which is recessed relative to the remainder of the bottom surface of the lead 150, extends along the entire length of the angled portion of each lead 150 which includes such angled portion, and further extends in generally co-planar relation to the etched surface 111 of the die pad 110. In FIG. 1A, the etched surface 151 in the bottom surface of each lead 150 is indicated by the condensed hatching which slopes downwardly from right to left. During the fabrication process for the semiconductor device 700 including the leadframe 100, the encapsulant material used to form the package body of the semiconductor device 700 is also able to flow over the etched surfaces 151 of the leads 150, thus resulting in substantial portions of the leads 150 being encapsulated by the package body of the semiconductor device 700 which enhances the bonding or mechanical interlock therebetween.

As is further apparent from FIGS. 1A and 1B, the manner in which the bottom surface of each of the leads 150 is etched facilitates the formation of a land portion 161 upon each of the leads 150. Within each set of the leads 150, the land portions 161 are segregated into first and second sets which are offset or staggered relative to each other. Additionally, as is apparent from FIG. 1B, the un-etched portion of the bottom surface of each lead 150 defines the generally planar bottom surface of the land portion 161 thereof which extends in generally co-planar relation to the bottom surface of the die pad 110 and the bottom surfaces of the first and second lands 141, 142. As indicated above, the top surfaces of the die pad 110, first and second lands 141, 142 and leads 150 extend in generally co-planar relation to each other as well. Thus, as will be discussed in more detail below, since the bottom surfaces the first and second lands 141, 142 and land portions 161 of the leads 150 are each exposed in and substantially flush with an exterior surface defined by the package body of the semiconductor device 700, they are electrically connectable to an underlying substrate such as a printed circuit board. In the process of fabricating the semiconductor device 700 as will be described in more detail below, the dambar 101 and the first and second support bars 131, 132 are each ultimately removed or singulated in a manner wherein the first and second lands 141, 142 and the leads 150 are electrically isolated from each other, and from the die pad 110 and tie bars 120 as well.

As further seen in FIG. 1A, each of the four sets of the leads 150 includes regions S where leads 150 are not formed, with each region S thus defining a gap between an adjacent pair of leads 150 which is of a size substantially exceeding the pitch between the remaining leads 150 in the same set. As is also apparent from FIG. 1A, each region S is generally aligned with a corresponding peripheral segment of a respective one of the first and second support bars 131, 132. As will be discussed in more detail below in relation to the fabrication process for the semiconductor device 700 including the leadframe 100, the regions S are devoid of any leads 150 since a saw blade which may ultimately used to facilitate the removal or singulation of the first and second support bars 131, 132 and portions of the tie bars 120 will pass through such regions S of the leadframe 100. Thus, if leads 150 were to be included in the regions S, such leads 150 would be removed during the sawing process used to facilitate the removal of the first and second support bars 131, 132. Thus, the leadframe 100 is formed so as not to include leads 150 in the regions S.

The leadframe 100 may be fabricated from a conventional metal material, such as copper, copper alloy, steel plated with copper, or a functional equivalent. However, those of ordinary skill in the art will recognize that the present invention is not limited to any particular material for the leadframe 100. Additionally, the number of lands 141, 142 and leads 150 shown in FIG. 1A is for illustrative purposes only, and may be modified according to application field. Along these lines, the lands 141, 142 and leads 150 may have designs or configurations varying from those shown in FIG. 1A without departing from the spirit and scope of the present invention. Additionally, though the lands 141, 142 and leads 150 are each shown as being segregated into four sets, it will be recognized that fewer sets thereof may be provided, and may be arranged along any combination of two or three of the peripheral sides of the die pad 110. Moreover, less than four tie bars 120 may be included in the leadframe 100, extending to respective corners of the die pad 110 in any combination. It is further contemplated that the leadframe 100 may be fabricated through the implementation of a chemical etching process or alternatively a mechanical stamping process.

Referring now to FIGS. 7A and 7B, the semiconductor device or package 700 as fabricated to include the leadframe 100 is shown in detail. As will be recognized by those of ordinary skill in the art, in the completed semiconductor device 700 shown in FIGS. 7A and 7B, the dambar 101 and the first and second support bars 131, 132, as well as portions of the tie bars 120, are each singulated or removed from the leadframe 100 to facilitate the electrical isolation of the various structural features of the leadframe 100 from each other. As indicated above, the dambar 101 and the first and second support bars 131, 132 are singulated in a manner wherein the first and second lands 141, 142 and the leads 150 are electrically isolated from each other, and from the die pad 110 and tie bars 120 as well.

In the semiconductor device 700, a semiconductor die 710 is attached to the top surface of the die pad 110 through the use of an adhesive layer 711. The semiconductor die 711 includes a plurality of bond pads which are disposed on the top surface thereof opposite the bottom surface adhered to the adhesive layer 711. The bond pads are used to deliver and receive electrical signals.

The semiconductor device 700 further comprises a plurality of conductive wires 720 which are used to electrically connect the bond pads of the semiconductor die 710 to respective ones of the lands 141, 142 and the leads 150. More particularly, as seen in FIG. 7A, the wires 720 are extended to the top surfaces of respective ones of the lands 141, 142 and the leads 150. The conductive wires 720 may be fabricated from aluminum, copper, gold, silver, or a functional equivalent. However, those of ordinary skill in the art will recognize that the present invention is not limited to any particular material for the wires 720. One or more conductive wires 720 may also be used to electrically connect one or more bond pads of the semiconductor die 710 directly to the die pad 110.

In the semiconductor device 700, the die pad 110, the tie bars 120, the lands 141, 142, the leads 150, the semiconductor die 710 and the conductive wires 720 are at least partially encapsulated or covered by an encapsulant material which, upon hardening, forms the package body 730 of the semiconductor device 700. More particularly, the package body 730 covers the entirety of the die pad 110 except for the bottom surface thereof which is circumvented by the etched surface 111. The package body 730 also covers the top surfaces of the lands 141, 142 and leads 150, as well as portions of the side surfaces thereof. The etched surfaces 151 of the leads 150 and the etched surfaces 121 of the tie bars 120 are also covered by the package body 730. However, the package body 730 does not cover the bottom surfaces of the first and second lands 141, 142 and the land portions 161, nor does the package body 730 cover the bottom surfaces of the tie bars 120 or the bottom surface of the die pad 110, as indicated above. As such, in the completed semiconductor device 700, the bottom surfaces of the die pad 110, tie bars 120 (which are not removed or singulated), first and second lands 141, 142 and land portions 161 of the leads 150 are exposed in and substantially flush with a generally planar bottom surface 733 defined by the package body 730. During the process of fabricating the semiconductor device 700, the bottom surfaces of the first and second support bars 131, 132 and the dambar 101 are also not covered by the package body 730 so that they may be removed from the leadframe 100.

Though the first and second support bars 131, 132 are partially covered by the package body 730, as indicated above, the bottom surfaces of the first and second support bars 131, 132 are exposed in the bottom surface 733 so that they, like the dambar 101, may be removed from the completed semiconductor device 700 as needed to facilitate the electrical isolation of various structural features thereof from each other. As shown in FIG. 7B, the removal of the first and second support bars 131, 132, which is may accomplished through the completion of a partial sawing or etching process which will be described in more detail below, facilitates the formation of a plurality of elongate trenches 731, 732 within the bottom surface 733 of the package body 730, such trenches 731, 732 extending in generally perpendicular relation to each other, and generally perpendicularly between an opposed pair of the side surfaces of the package body 730. As further shown in FIG. 7B, the trenches 731 formed as a result of the removal of at least portions of the first support bar 141 separate each set of the first lands 141 from a corresponding peripheral edge segment of the die pad 110. Similarly, the trenches 732 formed as a result of the removal of the second support bar 142 separate each set of the first lands 141 from a corresponding set of the second lands 142. The sawing or etching process used to facilitate the full or partial removal of the first and second support bars 141, 142 also facilitates the removal of portions of the tie bars 120 from the leadframe 100. Additionally, due to the manner in which the sawing or etching process is completed to facilitate the removal of the first and second support bars 141, 142, the trenches 731, 732 extend within the bottom surface 733 of the package body 730 through the above-described regions S of the leadframe 100. As previously explained, due to the passage of the trenches 731, 732 therethrough, the regions S are devoid of the leads 150 which would otherwise be removed during the process of fabricating the semiconductor device 700.

As indicated above, due to the structural attributes of the fully formed package body 730, the generally planar bottom surface of the die pad 110 is exposed in and substantially flush with the generally planar bottom surface 733 of the package body 730, as are the generally planar bottom surfaces of the first and second lands 141, 142, land portions 161 of the leads 150, and tie bars 120. As also indicated above, in order to complete the fabrication of the semiconductor device 700 to allow the same to assume the configuration shown in FIGS. 7A and 7B, the dambar 101 must be removed from the leadframe 100. In this regard, it is contemplated that a conventionally known debarring process may be implemented to remove the dambar 101. The completion of such debarring process results in each of the leads 150 defining an outer, distal end which is exposed in and substantially flush with a side surface defined by the package body 730.

In the semiconductor device 700, the first and second lands 141, 142 are exposed in the bottom surface 733 of the package body 730, as are the land portions 161 of the leads 150. As a result, the first and second lands 141, 142 and the land portions 161 are capable of being mounted to the surface of an underlying substrate such as a printed circuit board through the use of, for example, a soldering technique. Electrical signals are routed between the first and second lands 141, 142, the leads 150 and the semiconductor die 710 by the corresponding conductive wires 720. Side surface portions of the first lands 141 are also exposed in each of the trenches 731, 732, with side surface portions of the second lands 141 being exposed in the trench 732.

Figure 11:
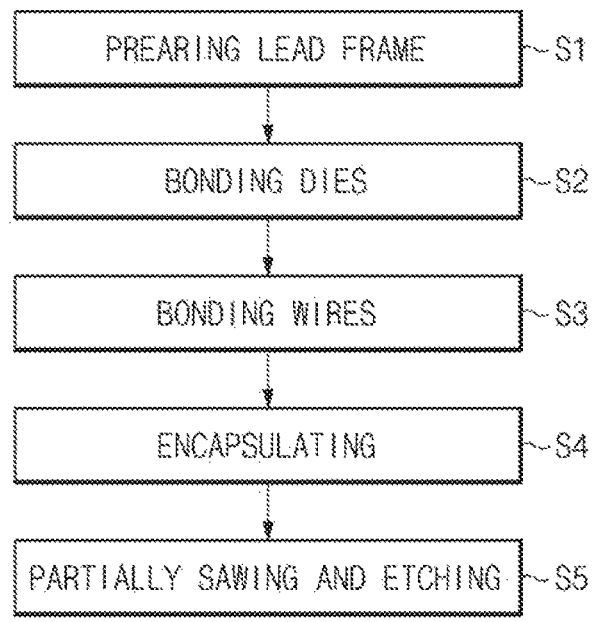
FIG. 11 is a flow chart illustrating an exemplary fabrication method for the semiconductor device shown in FIGS. 7A and 7B.

Referring now to FIG. 11, there is provided a flow chart which sets forth an exemplary method for fabricating the semiconductor device 700 of the present invention. The method comprises the steps of preparing the leadframe (S1), semiconductor die attachment (S2), wire bonding (S3), encapsulation (S4), and partial sawing and etching (S5). FIGS. 12A-12E provide illustrations corresponding to these particular steps, as will be discussed in more detail below.

Figure 12A:
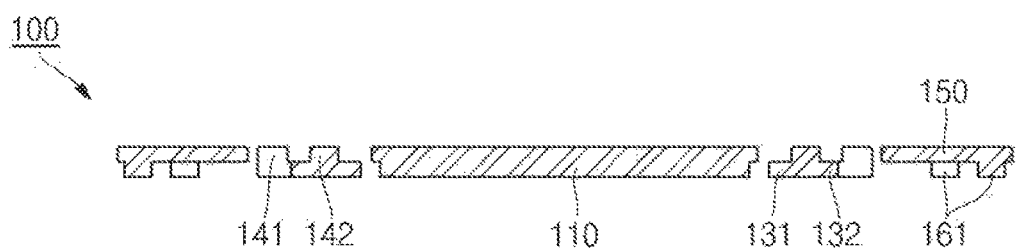
FIGS. 12A-12E are views illustrating an exemplary fabrication method for the semiconductor device shown in FIGS. 7A and 7B.
Figure 12B:
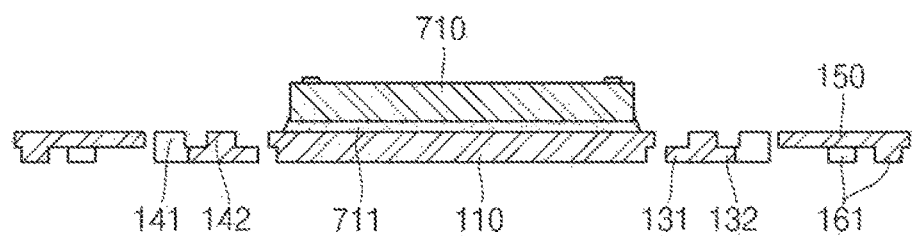

Referring now to FIG. 12A, in the initial step S1 of the fabrication process for the semiconductor device 700, the leadframe 100 having the above-described structural attributes is provided. Thereafter, as illustrated in FIG. 12B, step S2 is completed wherein the semiconductor die 710 having the bond pads is attached to the top surface of the die pad 110 of the leadframe 100 through the use of the adhesive layer 711. The adhesive layer 711 can be selected from well known liquid epoxy adhesives, adhesive films and adhesive tapes, as well as equivalents thereto.

Figure 12C:
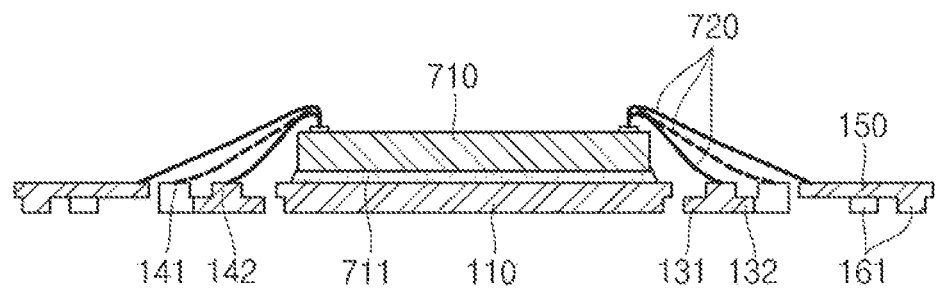

Referring now to FIG. 12C, in the next step S3 of the fabrication process, the conductive wires 720 are used to electrically interconnect the semiconductor die 710 to the leadframe 100 in the aforementioned manner. Specifically, the bond pads of the semiconductor die 710 are electrically connected to the top surfaces of the first and second lands 141, 142 and the leads 150. Though not shown, as indicated above, one or more conductive wires 720 may also be used to electrically connect one or more bond pads of the semiconductor die 710 directly to the die pad 110, allowing for the use of the die pad 110 as a ground region.

Figure 12D:
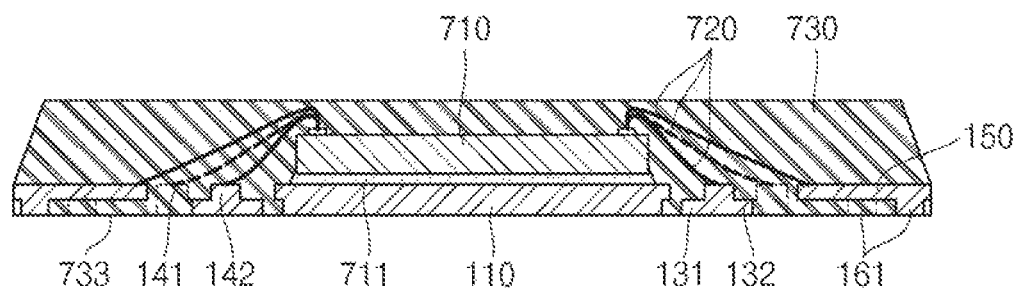

Referring now to FIG. 12D, in the next step S4 of the fabrication process for the semiconductor device 700, portions of the leadframe 100, the semiconductor die 710 and the conductive wires 720 are encapsulated with an encapsulant material which, upon hardening, forms the package body 730 of the semiconductor device 700. More particularly, the package body 730 covers the entirety of the die pad 110 except for the bottom surface thereof which is circumvented by the etched surface 111. The package body 730 also covers the top surfaces of the lands 141, 142 and leads 150, as well as portions of the side surfaces thereof. The etched surfaces 151 of the leads 150 and the etched surfaces 121 of the tie bars 120 are also covered by the package body 730. However, the package body 730 does not cover the bottom surfaces of the first and second lands 141, 142 and the land portions 161, nor does the package body 730 cover the bottom surfaces of the tie bars 120 or the bottom surface of the die pad 110, as indicated above. As such, in the completed semiconductor device 700, the bottom surfaces of the die pad 110, tie bars 120 (which are not removed or singulated), first and second lands 141, 142 and land portions 161 of the leads 150 are exposed in and substantially flush with a generally planar bottom surface 733 defined by the package body 730. The bottom surfaces of the first and second support bars 131, 132 and the dambar 101 are also not covered by the package body 730 so that they may be removed from the leadframe 100 in a subsequent step of the fabrication process.

Figure 12E:
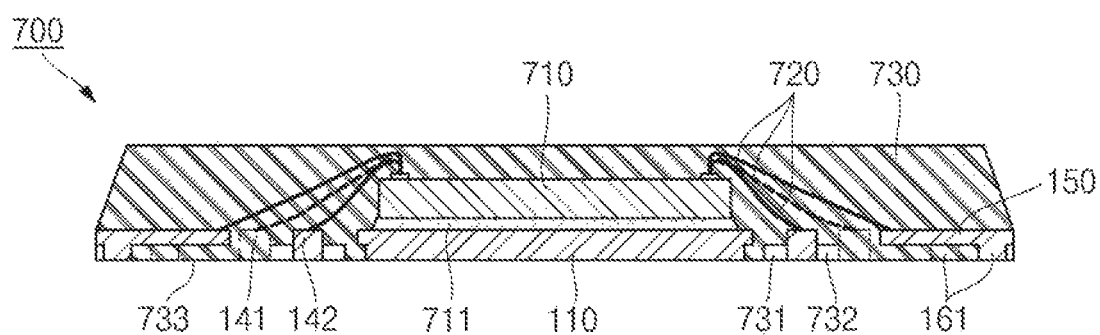

Referring now to FIG. 12E, in the next step S5 of the fabrication process for the semiconductor device 700, the removal of the first and second support bars 131, 132 and portions of the tie bars 120 is preferably facilitated by sawing with a blade, the trenches 731, 732 being formed as an artifact of such sawing process. The removal of the first and second support bars 131, 132 is needed to facilitate the electrical isolation of the first and second lands 141, 142 from each other, as well as from the die pad 110, tie bars 120 and leads 150. Additionally, the dambar 101 is trimmed or removed by cutting with a cutting tool so that the leads 150 are electrically isolated from each other, as well as the die pad 110 and tie bars 120. As previously explained, the dambar 101 is positioned outside of the package body 730 to allow for the removal thereof from the leadframe 100, and is removed by cutting the same with dambar cutting tool. As an alternative to the use of a sawing process to facilitate the removal of the first and second support bars 131, 132 and portions of the tie bars 120, it is contemplated that the leadframe 100 may be subjected to an etching process using a suitable etching solution. In this regard, the etching solution would be applied to the bottom surfaces of the first and second support bars 131, 132, and portions of the bottom surfaces of the tie bars 120, which are each exposed in the bottom surface 733 of the package body 730. The etching process, like the above-described sawing process, may be completed in a manner which facilitates the formation of the above-described trenches 731, 732.

Figure 2:
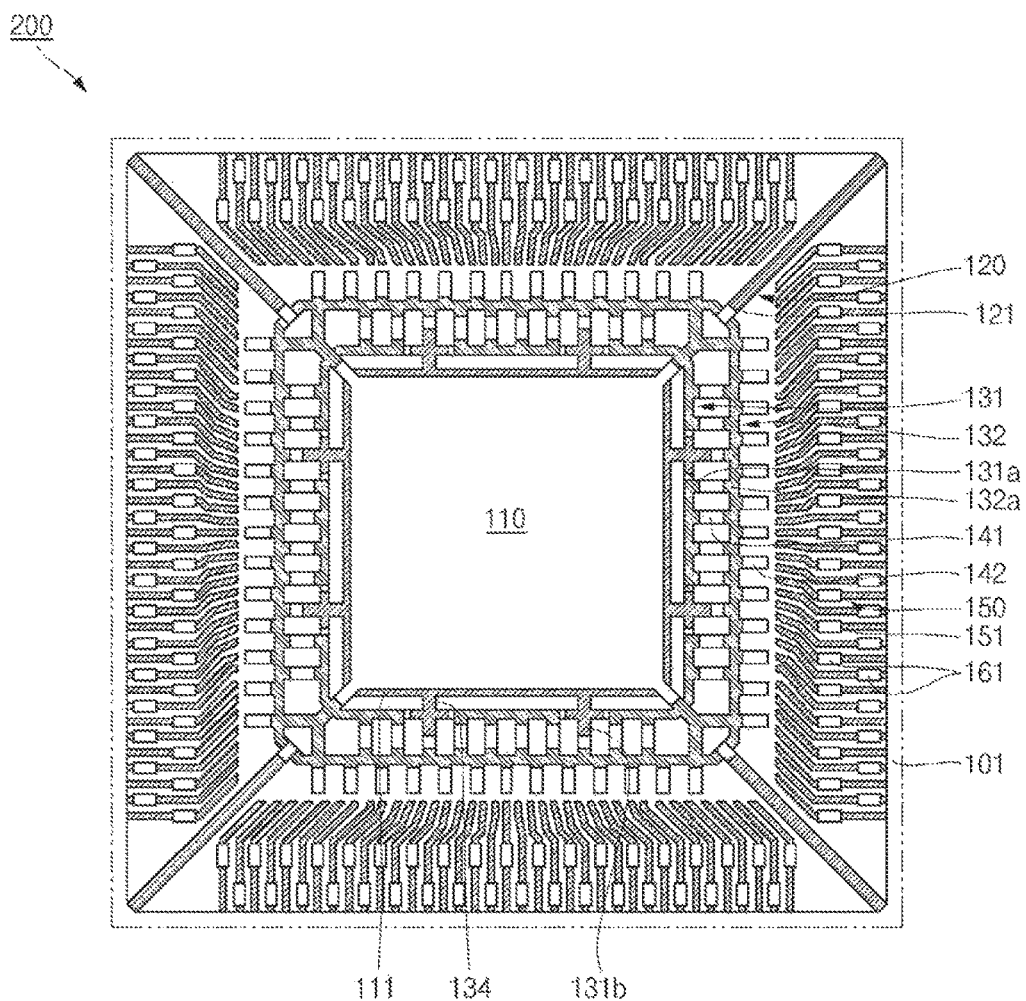
FIG. 2 is a top plan view of an unsingulated leadframe which is integrated into a semiconductor device or package constructed in accordance with a second embodiment of the present invention.
Figure 8:
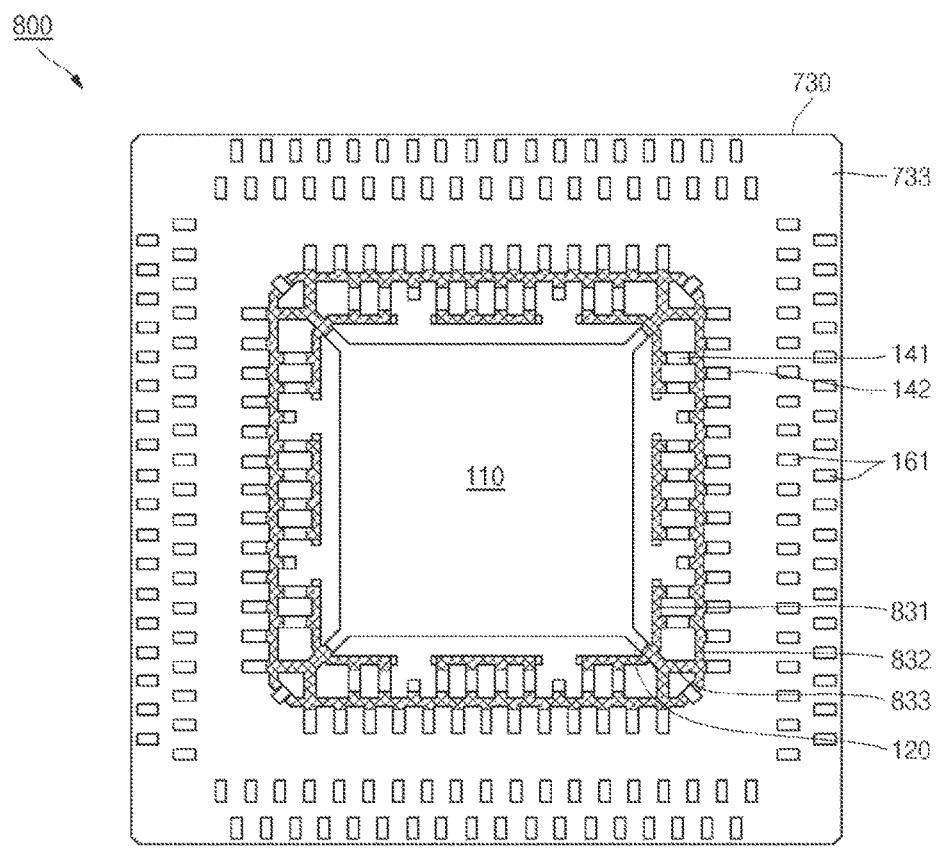
FIG. 8 is a bottom plan view of the semiconductor device of the second embodiment as fabricated to include the leadframe shown in FIG. 2.

Referring now to FIG. 2, there is shown an unsingulated leadframe 200 which is integrated into a semiconductor device 800 constructed in accordance with a second embodiment of the present invention, and shown in FIG. 8. The leadframe 200 is substantially similar in structure to the leadframe 100, with only the differences between the leadframes 100, 200 being described below.

One distinction between the leadframes 100, 200 lies in each set of the leads 150 included in the leadframe 200 not being formed to include the regions S shown and described above in relation to the leadframe 100 depicted in FIG. 1A. Thus, in the leadframe 200, the pitch or spacing between the leads 150 of each set is consistent. Another distinction lies in a portion of the top surface of each tie bar 120 being partially etched (e.g., half-etched) to define an etched surface, which is in addition to the etched surface 121. As seen in FIG. 2, the top etched surface of each tie bar 120, which is recessed relative to the remainder of the top surface of the tie bar 120, extends along the majority of the length of the inner linear portion thereof, and along the entirety of the triangular portion thereof. In FIG. 2, the etched surface in the top surface of each tie bar 120 is indicated by the condensed hatching which slopes downwardly from left to right. The top etched surface of each tie bar 120 extends in generally co-planar relation to the etched surface 111 of the die pad 110. However, as also seen in FIG. 2, the etched surface 121 of each tie bar 120 does not extend along the entire length of the outer linear portion thereof, as is the case in the leadframe 100. Rather, in the leadframe 200, one end of the etched surface 121 of each tie bar 120 terminates at the dambar 101, with the opposite end terminating just short of the triangular portion, and hence the aforementioned gap separating the inner and outer linear portions of each tie bar 120 from each other.

As indicated above, the semiconductor device 800 including the singulated leadframe 200 is shown in FIG. 8. In the process of fabricating the semiconductor device 800, the bottom surfaces of the first and second support bars 131, 132, and the bottom surfaces of the tie bars 120, are exposed in the bottom surface 733 of the package body 730 so that they, like the dambar 101, may be fully or partially removed from the completed semiconductor device 800 as needed to facilitate the electrical isolation of various structural features thereof from each other. As shown in FIG. 8, the removal of at least portions of the first support bar 131 through the completion of either partial sawing or etching process facilitates the formation of a plurality of trenches 831 in the bottom surface 733, the trenches 831 being disposed in spaced relation to each other and collectively defining a generally quadrangular (e.g., square) pattern. In the semiconductor device 800 shown in FIG. 8, the undisturbed regions of the bottom surface 733 of the package body 730 separating the trenches 831 from each other remain as a result from no sawing or etching process being completed at the portions of the bottom etched surface 131b included in each of the four peripheral segments of the first support bar 131. As further shown in FIG. 8, the removal of the second support bar 132 through the completion of a partial sawing or etching process facilitates the formation of four elongate trenches 832 in the bottom surface 733 of the package body 730, the trenches 832 also being arranged in a generally quadrangular (e.g., square) pattern. The removal of portions of each of the tie bars 120 is also accomplished through the completion of a partial sawing or etching process which facilitates the formation of four trenches 833 located at respective ones of the four corner regions of the die pad 110.

In the semiconductor device 800, the trenches 831 formed as a result of the removal of at least portions of the first support bar 141 separate each of the first lands 141 from a corresponding peripheral edge segment of the die pad 110. Similarly, the trenches 832 formed as a result of the removal of the second support bar 142 separate each set of the first lands 141 from a corresponding set of the second lands 142. Though the removal of portions of each of the tie bars 120 facilitates the formation of the trenches 833, the partial sawing or etching process which facilitates the formation of the trenches 833 is completed such that a small section of the bottom surface of each tie bar 120 remains exposed in and substantially flush with the bottom surface 733 of the package body 730. As seen in FIG. 8, such exposed portion of the bottom surface of each tie bar 120 is disposed between an adjacent pair of the trenches 832. Due to the manner in which the sawing or etching process is completed to facilitate the full or partial removal of the first and second support bars 141, 142 and the tie bars 120, none of the trenches 831, 832, 833 extends beyond the second lands 142 to the side surface of the package body 730. As a result, the first leads 150 in the leadframe 200 integrated into the semiconductor device 800 need not include the regions S as described above.

Figure 3:
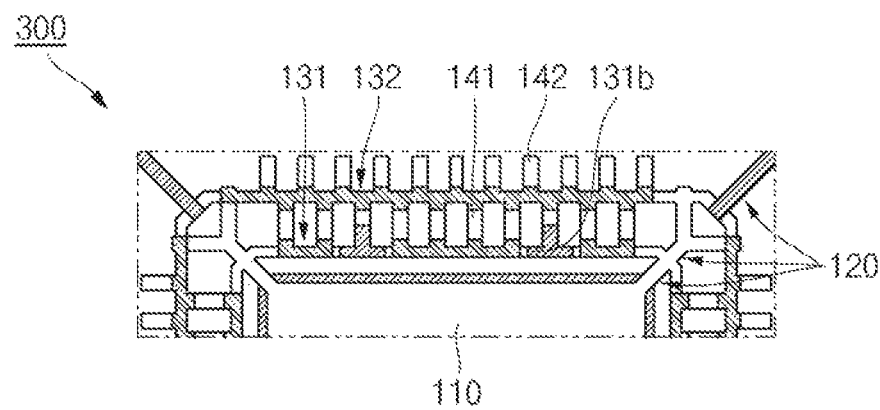
FIG. 3 is a partial top plan view of an unsingulated leadframe which is integrated into a semiconductor device or package constructed in accordance with a third embodiment of the present invention.

Referring now to FIG. 3, there is shown a portion of an unsingulated leadframe 300 which may be integrated into a semiconductor device constructed in accordance with a third embodiment of the present invention. The leadframe 300 is substantially similar in structure to the leadframe 100, with only the differences between the leadframes 100, 300 being described below.

The sole distinction between the leadframes 100, 300 lies in the omission of the auxiliary tie bars 134 in the leadframe 300. Thus, though the first support bar 131 in the leadframe 300 is integrally connected to the tie bars 120, it is not directly connected to the die pad 110. Those of ordinary skill in the art will recognize that the leadframe 200 shown in FIG. 2 may itself be modified to omit the auxiliary tie bars 134 in the manner shown in relation to the leadframe 300 in FIG. 3.

Figure 4:
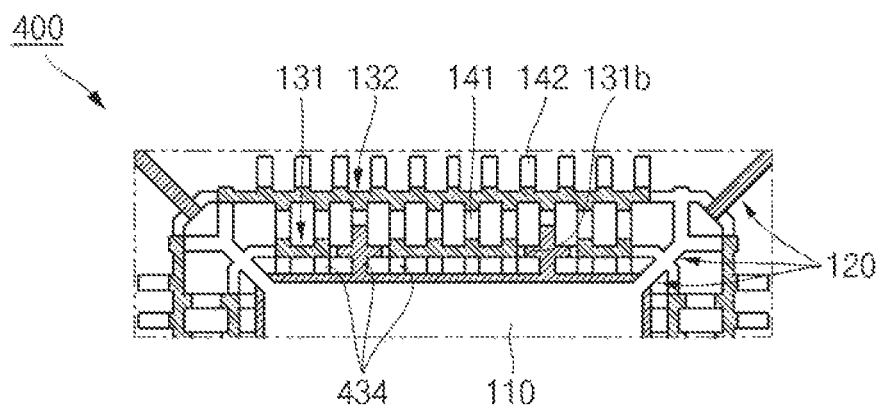
FIG. 4 is a partial top plan view of an unsingulated leadframe which is integrated into a semiconductor device or package constructed in accordance with a fourth embodiment of the present invention.

Referring now to FIG. 4, there is shown a portion of an unsingulated leadframe 400 which may be integrated into a semiconductor device constructed in accordance with a fourth embodiment of the present invention. The leadframe 400 is substantially similar in structure to the leadframe 100, with only the differences between the leadframes 100, 400 being described below.

In the leadframe 400, two auxiliary tie bars 134 are used to integrally connect each of the four peripheral segments of the first support bar 131 to a corresponding peripheral edge segment of the die pad 110. In the leadframe 400, more than two auxiliary tie bars 434 are used to integrally connect each peripheral segment of the first support bar 131 to the corresponding peripheral edge segment of the die pad 110. More particularly, as seen in FIG. 4, the number of auxiliary tie bars 434 used to integrally connect each peripheral segment of the first support bar 131 to the corresponding peripheral edge segment of the die pad 110 is equal to the number of first lands 141 of each set thereof. In this regard, as also seen in FIG. 4, the auxiliary tie bars 434 of each set thereof are substantially aligned with one of the first lands 141 of the corresponding set thereof. Though the two auxiliary tie bars 434 of each set which are aligned with the bottom etched surface 131b of the corresponding peripheral segment of the first support bar 131 also have an etched bottom surface as described above, the remaining auxiliary tie bars 434 of the same set are not etched.

Figure 5:
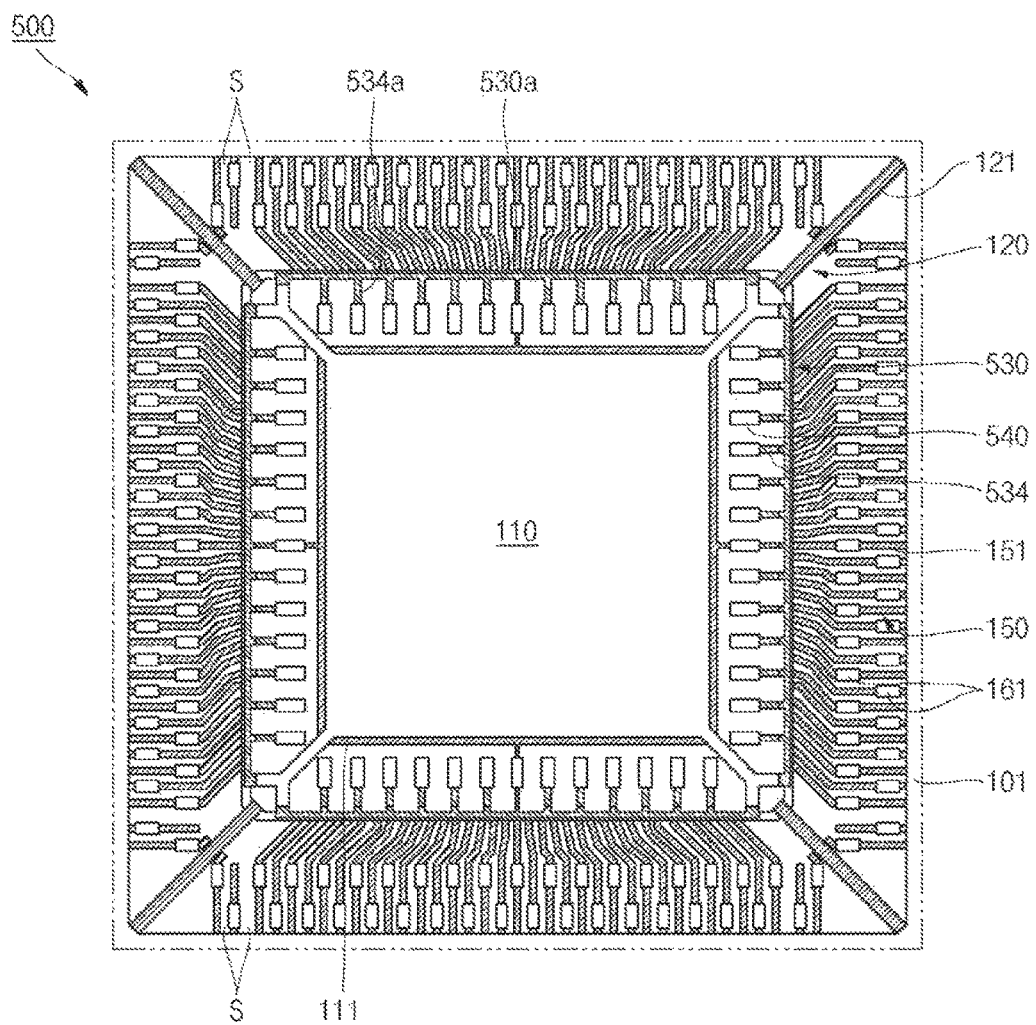
FIG. 5 is a top plan view of an unsingulated leadframe which is integrated into a semiconductor device or package constructed in accordance with a fifth embodiment of the present invention.
Figure 9A:
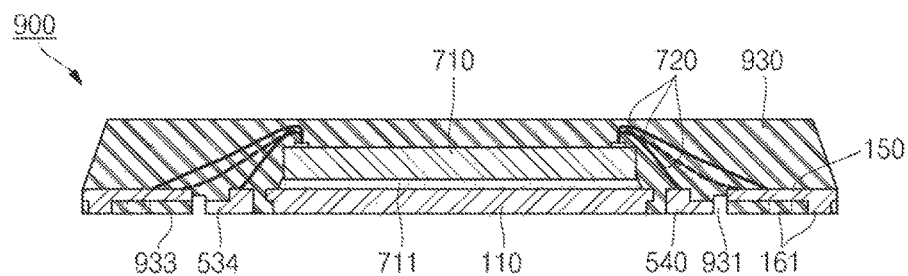
FIG. 9A is a cross-sectional view of the semiconductor device of the fifth embodiment as fabricated to include the leadframe shown in FIG. 5.
Figure 9B:
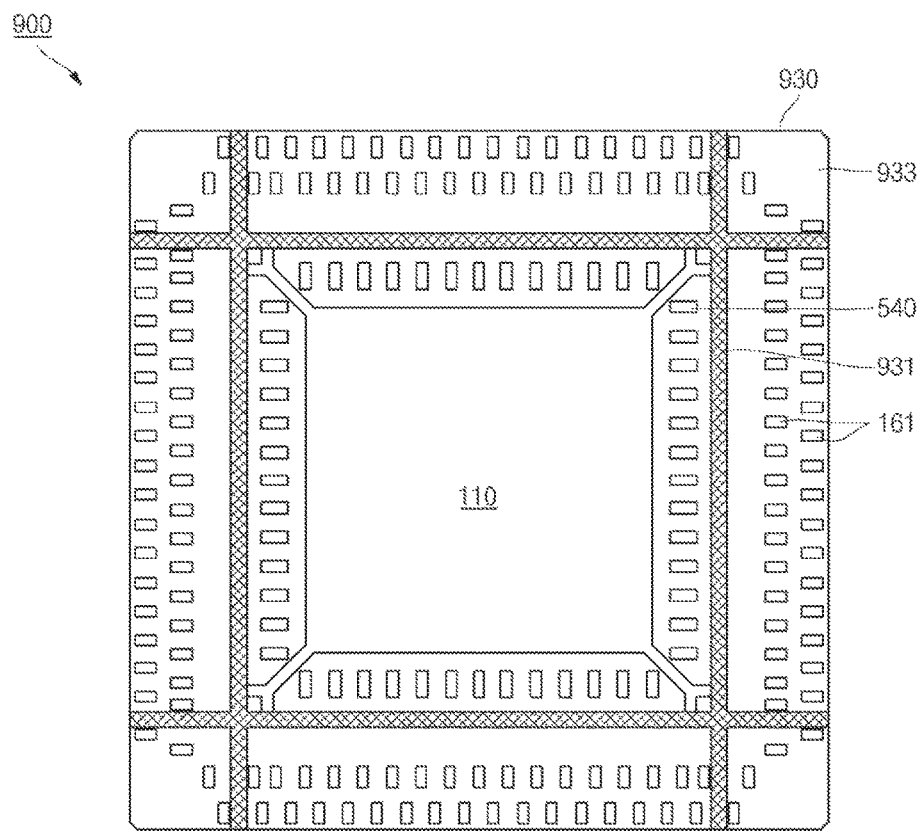
FIG. 9B is a bottom plan view of the semiconductor device of the fifth embodiment shown in FIG. 9A.

Referring now to FIG. 5, there is shown an unsingulated leadframe 500 which is integrated into a semiconductor device 900 constructed in accordance with a fifth embodiment of the present invention. The semiconductor device 900 is shown in FIGS. 9A and 9B.

As seen in FIG. 5, the leadframe 500 comprises a generally quadrangular (e.g., square) die paddle or die pad 110 which defines four peripheral edge segments. The die pad 110 defines opposed, generally planar top and bottom surfaces. As seen in FIG. 5, the die pad 110 of the leadframe 500 is not of uniform thickness. Rather, a peripheral portion of the bottom surface of the die pad 110 is partially etched (e.g., half-etched) to define an etched surface 111. More particularly, the etched surface 111, which is recessed relative to the remainder of the bottom surface of the die pad 110, is segregated into four segments, with each of these segments extending along a respective one of peripheral edge segments of the die pad 110 and between a respective pair of tie bars 120 of the leadframe 500 which are described in more detail below. In FIG. 5, which is a bottom plan view of the leadframe 500, the etched surface 111 in the bottom surface of the die pad 110 is indicated by the condensed hatching which slopes downwardly from right to left.

In the fabrication process for the semiconductor device 900 including the leadframe 500, a semiconductor die is attached to the top surface of the die pad 110 through the use of an adhesive layer, with an encapsulant material thereafter being applied to the semiconductor die and the leadframe 500 to form the package body of the semiconductor device 900. Advantageously, the etched surface 111 formed in the peripheral portion of the bottom surface of the die pad 110 as indicated above effectively increases the distance along which moisture must travel to reach the semiconductor die mounted to the top surface of the die pad 110. As a result, such semiconductor die is safely protected against moisture in the completed semiconductor device 900. Additionally, the flow of encapsulant material over the etched surface 111 during the formation of the package body of the semiconductor device 900 facilitates the creation of a mechanical interlock between the package body and the die pad 110.

Integrally connected to the die pad 110 are a plurality of tie bars 120. More particularly, the leadframe 500 includes four tie bars 120 which extend diagonally from respective ones of the four corner regions defined by the die pad 110. As seen in FIG. 5, the tie bars 120 are integrally connected to a generally quadrangular frame or dambar 101 which circumvents the die pad 110 and is disposed in spaced relation thereto. The tie bars 120 are identically configured to each other, and extend diagonally outwardly at predetermined lengths from respective ones of the corner regions of the die pad 110, with the integral connection of the tie bars 120 to the dambar 101 effectively supporting the die pad 110 within the interior of the dambar 101. However, as is apparent from FIG. 5, each of the tie bars 120 does not have an uninterrupted, linear configuration. Rather, each of the tie bars 120 defines inner and outer generally straight or linear portions which are separated from each other by a generally triangular portion, the inner linear portion being integrally connected to and extending from a respective corner region of the die pad 110, and the outer linear portion extending and being integrally connected to the dambar 101. As seen in FIG. 5, the triangular portion included in each dambar 120 effectively creates a gap or space separating the adjacent ends of the inner and outer linear portions thereof from each other.

Each of the tie bars 120 of the leadframe 500 defines opposed, generally planar top and bottom surfaces which extend in generally co-planar relation to respective ones of the top and bottom surface of the die pad 110. However, a portion of the bottom surface of each tie bar 120 is preferably partially etched (e.g., half-etched) to define an etched surface 121. The etched surface 121 of each tie bar 120, which is recessed relative to the remainder of the bottom surface of the tie bar 120, extends along the entire length of the outer linear portion thereof. As such, one end of the etched surface 121 of each tie bar 120 terminates at the dambar 101, with the opposite end terminating at the aforementioned gap separating the inner and outer linear portions of each tie bar 120 from each other. The etched surface 121 of each tie bar 120 extends in generally co-planar relation to the etched surface 111 of the die pad 110. In FIG. 5, the etched surface 121 in the bottom surface of each tie bar 120 is indicated by the condensed hatching which slopes downwardly from right to left. During the fabrication process for the semiconductor device 900 including the leadframe 500, the encapsulant material used to form the package body of the semiconductor device 900 is also able to flow over the etched surfaces 121 of the tie bars 120, thus resulting in the outer linear portions of the tie bars 120 being encapsulated by the package body of the semiconductor device 900 which enhances the bonding or mechanical interlock therebetween.

As indicated above, the tie bars 120 are integrally connected to the dambar 101 which circumvents the die pad 110. In the leadframe 500, the dambar 101 is provided in the form of a substantially quadrangular (e.g., square) ring which interconnects the distal ends of the tie bars 120. As seen in FIG. 5, the dambar 101 defines four peripheral segments which extend in spaced, generally parallel relation to respective ones of the peripheral edge segments of the die pad 110. In a fabrication process for the semiconductor package 900, the dambar 101 is singulated or removed from the leadframe 500 to electrically isolate other structural features of the leadframe 500 from each other.

The leadframe 500 further comprises a support bar 530 which is integrally connected to the tie bars 120 and circumvents the die pad 110. More particularly, as seen in FIG. 5, the support bar 530 has a generally quadrangular (e.g., square) configuration and defines four peripheral segments which extend in spaced, generally parallel relation to respective ones of the peripheral edge segments of the die pad 110. Thus, the support bar 530 is concentrically positioned between the die pad 110 and the frame 101. Each peripheral segment of the support bar 530 is integrally connected to and extends between a corresponding adjacent pair of the tie bars 120.

In the leadframe 500, the support bar 530 defines opposed, generally planar top and bottom surfaces which extends in generally co-planar relation to respective ones of the top and bottom surfaces of the die pad 110. However, the support bar 530 is not of uniform thickness. Rather, a portion of the top surface of the support bar 530 within each of the four peripheral segments thereof is partially etched (e.g., half-etched) to define an etched surface 530a. Thus, the etched surface 530a of the support bar 530 is recessed relative to the top surface thereof and is segregated into four segments which extend within respective ones of the four peripheral segments of the support bar 530. In FIG. 5, which is a bottom plan view of the leadframe 100 as indicated above, the etched surface 530a of the support bar 530 is indicated by the condensed hatching which slopes downwardly from left to right (rather than from right to left). In the leadframe 500, the etched surface 530a preferably extends in generally coplanar relation to the etched surface 111 of the die pad 110.

The leadframe 500 of the present invention further comprises a plurality of lands 540 which are each integrally connected to the support bar 530, and protrude inwardly toward the die pad 110. More particularly, as seen in FIG. 5, the lands 540 are segregated into four sets, with each set of the lands 540 protruding inwardly from a respective one of the peripheral segments of the support bar 530 toward a corresponding peripheral edge segment of the die pad 110. The lands 540 of each set are arrange at a predetermined pitch and protrude perpendicularly inward at a predetermined length from a respective one of the peripheral segments of the support bar 530. Each of the lands 540 has a generally planar top surface which extends in generally co-planar relation to the top surface of the die pad 110, and a generally planar bottom surface which extends in generally co-planar relation to the bottom surface of the die pad 110.

In the leadframe 500, the integral connection of each of the lands 540 of each set thereof to a corresponding one of the peripheral segments of the support bar 530 is facilitated by an intervening auxiliary support bar 534. Thus, the auxiliary support bars 534 of the leadframe 500 are also segregated into four sets, with each auxiliary support bar 534 of each set being integrally connected to and extending between one of the lands 540 of the corresponding set thereof and a corresponding one of the peripheral segments of the support bar 530. In the leadframe 500, each of the auxiliary support bars 534 is subjected to a partial etching process (e.g., is half-etched) to define a top etched surface 534a. In FIG. 5, which is a bottom plan view of the leadframe 500 as indicated above, the etched surface 534a of each auxiliary support bar 534 is indicated by the condensed hatching which slopes downwardly from left to right. The etched surfaces 534a of the auxiliary support bars 534 are preferably substantially flush or co-planar with the etched surface 111 of the die pad 110. During the fabrication process for the semiconductor device 900 including the leadframe 500, the encapsulant material used to form the package body of the semiconductor device 900 is also able to flow over the etched surfaces 534a of the auxiliary support bars 534.

The leadframe 500 constructed in accordance with the present invention further comprises a plurality of leads 150, the majority of which are integrally connected to and extend between the support bar 530 and the dambar 101. More particularly, the leads 150, like the lands 540 are preferably segregated into four sets, with each set of the leads 150 extending between an adjacent pair of the tie bars 120. The leads 150 of each set also extend toward a corresponding peripheral edge segment of the die pad 110, and are arranged at a predetermined pitch. As further seen in FIG. 5, two of the leads 150 of each set have a generally linear configuration, and extend generally perpendicularly from a corresponding peripheral segment of the dambar 101. However, the remaining leads 150 of each set each preferably have an angled configuration so as to extend toward a respective one of the peripheral edge segments of the die pad 110. Within each set of the leads 150, all but four are integrally connected to both the support bar 530 and dambar 101. In this regard, only the two outermost pairs of leads 150 of each (each such pair including one of the liner leads 150) is integrally connected to only the dambar 101.

Each of the leads 150 defines opposed, generally planar top and bottom surfaces which extend in generally co-planar relation to respective ones of the top and bottom surfaces of the die pad 110. However, a portion of the bottom surface of each lead 150 is preferably partially etched (e.g., half-etched) to define an etched surface 151. The etched surface 151 of each lead 150, which is recessed relative to the remainder of the bottom surface of the lead 150, extends along the entire length of the angled portion of each lead 150 which includes such angled portion, and further extends in generally co-planar relation to the etched surface 111 of the die pad 110. In FIG. 5, the etched surface 151 in the bottom surface of each lead 150 is indicated by the condensed hatching which slopes downwardly from right to left. During the fabrication process for the semiconductor device 900 including the leadframe 500, the encapsulant material used to form the package body of the semiconductor device 900 is also able to flow over the etched surfaces 151 of the leads 150, thus resulting in substantial portions of the leads 150 being encapsulated by the package body of the semiconductor device 900 which enhances the bonding or mechanical interlock therebetween.

As is further apparent from FIG. 5, the manner in which the bottom surface of each of the leads 150 is etched facilitates the formation of a land portion 161 upon each of the leads 150. Within each set of the leads 150, the land portions 161 are segregated into first and second sets which are offset or staggered relative to each other. Additionally, as is apparent from FIG. 5, the un-etched portion of the bottom surface of each lead 150 defines the generally planar bottom surface of the land portion 161 thereof which extends in generally co-planar relation to the bottom surface of the die pad 110 and the bottom surfaces of the lands 540. As indicated above, the top surfaces of the die pad 110, lands 540 and leads 150 extend in generally co-planar relation to each other as well. Thus, as will be discussed in more detail below, since the bottom surfaces the lands 540 and land portions 161 of the leads 150 are each exposed in and substantially flush with an exterior surface defined by the package body of the semiconductor device 900, they are electrically connectable to an underlying substrate such as a printed circuit board. In the process of fabricating the semiconductor device 900, the dambar 101 and the support bar 530 are each ultimately removed or singulated in a manner wherein the lands 540 and the leads 150 are electrically isolated from each other, and from the die pad 110 and tie bars 120 as well.

As further seen in FIG. 5, each of the four sets of the leads 150 includes regions S where leads 150 are not formed, with each region S thus defining a gap between an adjacent pair of leads 150 which is of a size substantially exceeding the pitch between the remaining leads 150 in the same set. As is also apparent from FIG. 5, each region S is generally aligned with a corresponding peripheral segment the support bar 530. As will be discussed in more detail below, the regions S are devoid of any leads 150 since a saw blade which may ultimately used to facilitate the removal or singulation of the support bar 530 and portions of the tie bars 120 will pass through such regions S of the leadframe 500. Thus, if leads 150 were to be included in the regions S, such leads 150 would be removed during the sawing process used to facilitate the removal of the support bar 530. Thus, the leadframe 500 is formed so as not to include leads 150 in the regions S.

The leadframe 500 may be fabricated from a conventional metal material, such as copper, copper alloy, steel plated with copper, or a functional equivalent. However, those of ordinary skill in the art will recognize that the present invention is not limited to any particular material for the leadframe 100. Additionally, the number of lands 540 and leads 150 shown in FIG. 5 is for illustrative purposes only, and may be modified according to application field. Along these lines, the lands 540 and leads 150 may have designs or configurations varying from those shown in FIG. 5 without departing from the spirit and scope of the present invention. Additionally, though the lands 540 and leads 150 are each shown as being segregated into four sets, it will be recognized that fewer sets thereof may be provided, and may be arranged along any combination of two or three of the peripheral sides of the die pad 110. Moreover, less than four tie bars 120 may be included in the leadframe 500, extending to respective corners of the die pad 110 in any combination. It is further contemplated that the leadframe 500 may be fabricated through the implementation of a chemical etching process or alternatively a mechanical stamping process.

Referring now to FIGS. 9A and 9B, the semiconductor device or package 900 as fabricated to include the leadframe 500 is shown in detail. As will be recognized by those of ordinary skill in the art, in the completed semiconductor device 900 shown in FIGS. 9A and 9B, the dambar 101 and the support bar 530, as well as portions of the tie bars 120, are each singulated or removed from the leadframe 500 to facilitate the electrical isolation of the various structural features of the leadframe 500 from each other. As indicated above, the dambar 101 and the support bar 530 are singulated in a manner wherein the lands 540 and the leads 150 are electrically isolated from each other, and from the die pad 110 and tie bars 120 as well.

In the semiconductor device 900, a semiconductor die 710 is attached to the top surface of the die pad 110 through the use of an adhesive layer 711. The semiconductor die 711 includes a plurality of bond pads which are disposed on the top surface thereof opposite the bottom surface adhered to the adhesive layer 711. The bond pads are used to deliver and receive electrical signals.

The semiconductor device 900 further comprises a plurality of conductive wires 720 which are used to electrically connect the bond pads of the semiconductor die 710 to respective ones of the lands 540 and the leads 150. More particularly, as seen in FIG. 9A, the wires 720 are extended to the top surfaces of respective ones of the lands 540 and the leads 150. The conductive wires 720 may be fabricated from aluminum, copper, gold, silver, or a functional equivalent. However, those of ordinary skill in the art will recognize that the present invention is not limited to any particular material for the wires 720. One or more conductive wires 720 may also be used to electrically connect one or more bond pads of the semiconductor die 710 directly to the die pad 110.

In the semiconductor device 900, the die pad 110, the tie bars 120, the lands 540, the leads 150, auxiliary support bars 534, the semiconductor die 710 and the conductive wires 720 are at least partially encapsulated or covered by an encapsulant material which, upon hardening, forms the package body 930 of the semiconductor device 900. More particularly, the package body 930 covers the entirety of the die pad 110 except for the bottom surface thereof which is circumvented by the etched surface 111. The package body 930 also covers the top surfaces of the lands 540 and leads 150, as well as portions of the side surfaces thereof. The etched surfaces 151 of the leads 150 and the etched surfaces 121 of the tie bars 120 are also covered by the package body 930. However, the package body 930 does not cover the bottom surfaces of the lands 540, the auxiliary support bars 534, and the land portions 161, nor does the package body 930 cover the bottom surfaces of the tie bars 120 or the bottom surface of the die pad 110, as indicated above. As such, in the completed semiconductor device 900, the bottom surfaces of the die pad 110, tie bars 120 (which are not removed or singulated), lands 540 and land portions 161 of the leads 150 are exposed in and substantially flush with a generally planar bottom surface 933 defined by the package body 930. During the process of fabricating the semiconductor device 900, the bottom surface of the support bar 530 and the dambar 101 are also not covered by the package body 930 so that they may be removed from the leadframe 500.

Though the support bar 530 is partially covered by the package body 930, as indicated above, the bottom surface thereof is exposed in the bottom surface 933 so that it, like the dambar 101, may be removed from the completed semiconductor device 900 as needed to facilitate the electrical isolation of various structural features thereof from each other. As shown in FIG. 9B, the removal of the support bar 530, which may accomplished through the completion of a partial sawing or etching process, facilitates the formation of a plurality of elongate trenches 931 within the bottom surface 933 of the package body 930, such trenches 931 extending in generally perpendicular relation to each other, and generally perpendicularly between an opposed pair of the side surfaces of the package body 930. As further shown in FIG. 9B, the trenches 931 formed as a result of the removal of the support bar 540 separate each set of the 540 lands 141 from a corresponding set of the leads 150. The sawing or etching process used to facilitate the removal of the support bar 530 also facilitates the removal of portions of the tie bars 120 from the leadframe 500. Additionally, due to the manner in which the sawing or etching process is completed to facilitate the removal of the support bar 530, the trenches 931 extend within the bottom surface 933 of the package body 930 through the above-described regions S of the leadframe 500. As previously explained, due to the passage of the trenches 931 therethrough, the regions S are devoid of the leads 150 which would otherwise be removed during the process of fabricating the semiconductor device 900. The sawing or etching process used to facilitate the removal of the support bar 530 also facilitates the removal of portions of each of the auxiliary support bars 534 from the leadframe 500.

As indicated above, due to the structural attributes of the fully formed package body 930, the generally planar bottom surface of the die pad 110 is exposed in and substantially flush with the generally planar bottom surface 933 of the package body 930, as are the generally planar bottom surfaces of the lands 540, land portions 161 of the leads 150, and tie bars 120. As also indicated above, in order to complete the fabrication of the semiconductor device 900 to allow the same to assume the configuration shown in FIGS. 9A and 9B, the dambar 101 must be removed from the leadframe 500. In this regard, it is contemplated that a conventionally known debarring process may be implemented to remove the dambar 101. The completion of such debarring process results in each of the leads 150 defining an outer, distal end which is exposed in and substantially flush with a side surface defined by the package body 930.

In the semiconductor device 900, the lands 540 are exposed in the bottom surface 933 of the package body 930, as are the land portions 161 of the leads 150. As a result, the lands 540 and the land portions 161 are capable of being mounted to the surface of an underlying substrate such as a printed circuit board through the use of, for example, a soldering technique. Electrical signals are routed between the lands 540, the leads 150 and the semiconductor die 710 by the corresponding conductive wires 720. As seen in FIG. 9A, portions of the auxiliary support bars 534 are exposed in the trenches 931, and in the bottom surface 933 of the package body 930.

Figure 6:
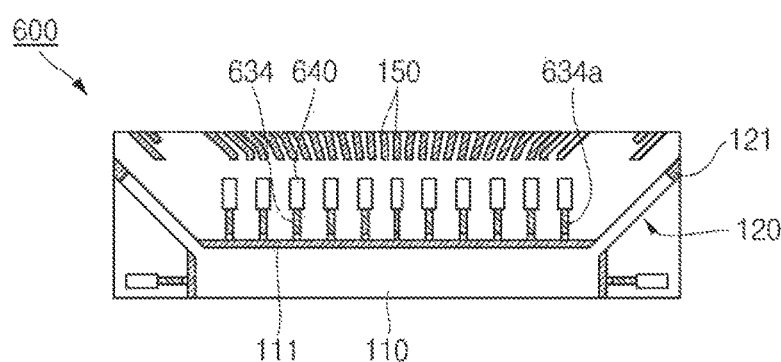
FIG. 6 is a partial top plan view of an unsingulated leadframe which is integrated into a semiconductor device or package constructed in accordance with a sixth embodiment of the present invention.
Figure 10A:
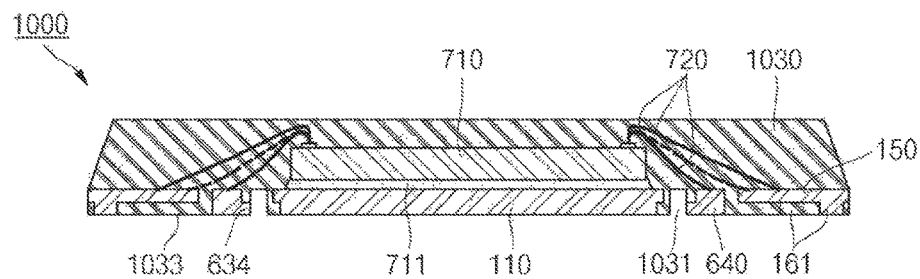
FIG. 10A is a cross-sectional view of the semiconductor device of the sixth embodiment as fabricated to include the leadframe shown in FIG. 6.
Figure 10B:
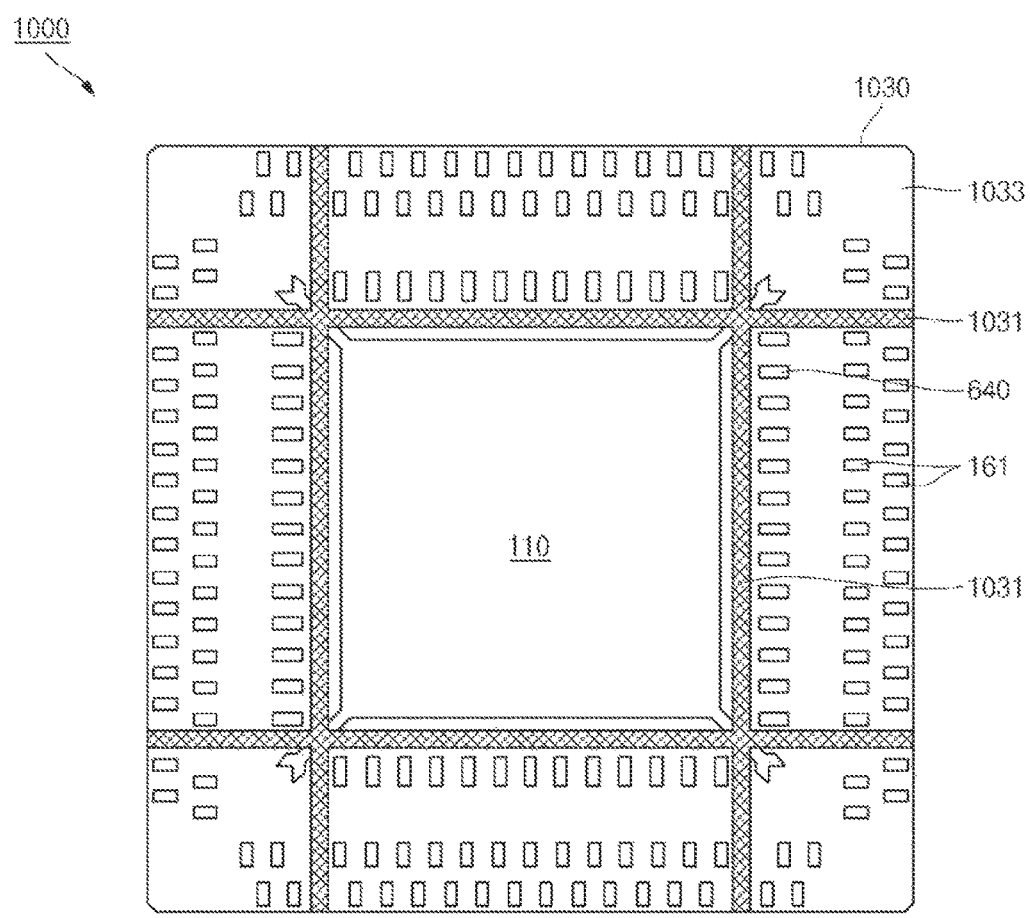
FIG. 10B is a bottom plan view of the semiconductor device of the sixth embodiment shown in FIG. 10A.

Referring now to FIG. 6, there is shown a portion of an unsingulated leadframe 600 which is integrated into a semiconductor device 1000 constructed in accordance with a sixth embodiment of the present invention. The semiconductor device 1000 is shown in FIGS. 10A and 10B.

As seen in FIG. 6, the leadframe 600 comprises a generally quadrangular (e.g., square) die paddle or die pad 110 which is identically configured to the die pad 110 of the above-described leadframe 500, and includes the etched surface 111. Integrally connected to the die pad 110 are a plurality of tie bars 120. More particularly, the leadframe 600 includes four tie bars 120 which extend diagonally from respective ones of the four corner regions defined by the die pad 110. The tie bars 120 are integrally connected to a generally quadrangular frame or dambar which circumvents the die pad 110 and is disposed in spaced relation thereto. The tie bars 120 are identically configured to each other, and extend diagonally outwardly at predetermined lengths from respective ones of the corner regions of the die pad 110, with the integral connection of the tie bars 120 to the dambar effectively supporting the die pad 110 within the interior of the dambar.

Each of the tie bars 120 of the leadframe 600 defines opposed, generally planar top and bottom surfaces which extend in generally co-planar relation to respective ones of the top and bottom surface of the die pad 110. However, a portion of the bottom surface of each tie bar 120 is preferably partially etched (e.g., half-etched) to define an etched surface 121. One end of the etched surface 121 of each tie bar 120, which is recessed relative to the remainder of the bottom surface of the tie bar 120, terminates at the dambar. The etched surface 121 of each tie bar 120 extends in generally co-planar relation to the etched surface 111 of the die pad 110. In FIG. 6, the etched surface 121 in the bottom surface of each tie bar 120 is indicated by the condensed hatching which slopes downwardly from right to left. During the fabrication process for the semiconductor device 1000 including the leadframe 600, the encapsulant material used to form the package body of the semiconductor device 1000 is also able to flow over the etched surfaces 121 of the tie bars 120 which enhances the bonding or mechanical interlock therebetween.

The leadframe 600 of the present invention further comprises a plurality of lands 640 which are each integrally connected to the die pad 110. More particularly, as seen in FIG. 6, the lands 640 are segregated into four sets, with each set of the lands 640 extending along a respective one of the peripheral edge segments of the die pad 110. The lands 640 of each set are arrange at a predetermined pitch and are of a predetermined length. Each of the lands 640 has a generally planar top surface which extends in generally co-planar relation to the top surface of the die pad 110, and a generally planar bottom surface which extends in generally co-planar relation to the bottom surface of the die pad 110.

In the leadframe 600, the integral connection of each of the lands 640 of each set thereof to a corresponding one of the peripheral edge segments of the die pad 110 is facilitated by an intervening auxiliary support bar 634. Thus, the auxiliary support bars 634 of the leadframe 600 are also segregated into four sets, with each auxiliary support bar 634 of each set being integrally connected to and extending between one of the lands 640 of the corresponding set thereof and a corresponding one of the peripheral edge segments of the die pad 110. In the leadframe 600, each of the auxiliary support bars 634 is subjected to a partial etching process (e.g., is half-etched) to define a top etched surface 634a. In FIG. 6, which is a bottom plan view of the leadframe 600 as indicated above, the etched surface 634a of each auxiliary support bar 634 is indicated by the condensed hatching which slopes downwardly from left to right. The etched surfaces 634a of the auxiliary support bars 634 are preferably substantially flush or co-planar with the etched surface 111 of the die pad 110.

The leadframe 600 constructed in accordance with the present invention further comprises a plurality of leads 150 which are integrally connected to the dambar and extend inwardly toward the die pad 110 in spaced relation thereto. The leads 150 of the leadframe 600 are identically configured to and arranged in the similar pattern as the leads 150 of the above-described leadframe 100, though the positioning of the regions S in the leadframe 600 is varied from that shown in FIG. 1A in relation to the leadframe 100. As such, each of the leads 150 in the leadframe 600 includes the etched surface 151, as well as the land portion 161, with the land portions 161 within each set of the leads 150 being segregated into first and second sets which are offset or staggered relative to each other. The leadframe 600 may also be fabricated from the same materials or with the same variants described above in relation to the leadframe 100.

Referring now to FIGS. 10A and 10B, the semiconductor device or package 1000 as fabricated to include the leadframe 600 is shown in detail. As will be recognized by those of ordinary skill in the art, in the completed semiconductor device 1000 shown in FIGS. 10A and 10B, the dambar, as well as portions of the auxiliary support bars 634 and tie bars 120, are each singulated or removed from the leadframe 600 to facilitate the electrical isolation of the various structural features of the leadframe 600 from each other. In this regard, the dambar and the auxiliary support bars 634 are singulated in a manner wherein the lands 640 and the leads 150 are electrically isolated from each other, and from the die pad 110 and tie bars 120 as well.

In the semiconductor device 1000, a semiconductor die 710 is attached to the top surface of the die pad 110 through the use of an adhesive layer 711. The semiconductor die 711 includes a plurality of bond pads which are disposed on the top surface thereof opposite the bottom surface adhered to the adhesive layer 711. The bond pads are used to deliver and receive electrical signals.

The semiconductor device 1000 further comprises a plurality of conductive wires 720 which are used to electrically connect the bond pads of the semiconductor die 710 to respective ones of the lands 640 and the leads 150. More particularly, as seen in FIG. 10A, the wires 720 are extended to the top surfaces of respective ones of the lands 640 and the leads 150. The conductive wires 720 may be fabricated from aluminum, copper, gold, silver, or a functional equivalent. However, those of ordinary skill in the art will recognize that the present invention is not limited to any particular material for the wires 720. One or more conductive wires 720 may also be used to electrically connect one or more bond pads of the semiconductor die 710 directly to the die pad 110.

In the semiconductor device 1000, the die pad 110, the tie bars 120, the lands 640, the leads 150, the auxiliary support bars 634, the semiconductor die 710 and the conductive wires 720 are at least partially encapsulated or covered by an encapsulant material which, upon hardening, forms the package body 1030 of the semiconductor device 1000. More particularly, the package body 1030 covers the entirety of the die pad 110 except for the bottom surface thereof which is circumvented by the etched surface 111. The package body 1030 also covers the top surfaces of the lands 640 and leads 150, as well as portions of the side surfaces thereof.

The etched surfaces 151 of the leads 150 and the etched surfaces 121 of the tie bars 120 are also covered by the package body 1030, as are the etched surfaces 634a of the auxiliary support bars 634. However, the package body 1030 does not cover the bottom surfaces of the lands 640 and the land portions 161, nor does the package body 1030 cover the bottom surfaces of the tie bars 120 or the bottom surface of the die pad 110, as indicated above. As such, in the completed semiconductor device 1000, the bottom surfaces of the die pad 110, tie bars 120 (which are not removed or singulated), lands 640 and land portions 161 of the leads 150 are exposed in and substantially flush with a generally planar bottom surface 1033 defined by the package body 1030. During the process of fabricating the semiconductor device 1000, the dambar is also not covered by the package body 1030 so that it may be removed from the leadframe 600.

Though the top etched surfaces 634a of the auxiliary support bars 634 are covered by the package body 1030, the bottom surfaces thereof are exposed in and substantially flush with the bottom surface 1033 of the package body 1030 so that they may also be at least partially removed from the completed semiconductor device 1000 as needed to facilitate the electrical isolation of various structural features thereof from each other. As shown in FIGS. 10A and 10B, the removal of the auxiliary support bars 634, which may accomplished through the completion of a partial sawing or etching process, facilitates the formation of a plurality of elongate trenches 1031 within the bottom surface 1033 of the package body 1030, such trenches 1031 extending in generally perpendicular relation to each other, and generally perpendicularly between an opposed pair of the side surfaces of the package body 1030. As further shown in FIG. 10B, the trenches 1031 formed as a result of the removal of the auxiliary support bars 634 separate each set of the lands 640 from a corresponding one of the peripheral edge segments of the die pad 110. The sawing or etching process used to facilitate the removal of the auxiliary support bars 634 also facilitates the removal of portions of the tie bars 120 from the leadframe 600. Additionally, due to the manner in which the sawing or etching process is completed to facilitate the removal of the auxiliary support bars 634, the trenches 1031 extend within the bottom surface 1033 of the package body 1030 through the above-described regions S of the leadframe 600. As previously explained, due to the passage of the trenches 1031 therethrough, the regions S are devoid of the leads 150 which would otherwise be removed during the process of fabricating the semiconductor device 1000.

As indicated above, due to the structural attributes of the fully formed package body 1030, the generally planar bottom surface of the die pad 110 is exposed in and substantially flush with the generally planar bottom surface 1033 of the package body 1030, as are the generally planar bottom surfaces of the lands 640, land portions 161 of the leads 150, and tie bars 120. As also indicated above, in order to complete the fabrication of the semiconductor device 1000 to allow the same to assume the configuration shown in FIGS. 10A and 10B, the dambar must be removed from the leadframe 600. In this regard, it is contemplated that a conventionally known debarring process may be implemented to remove the dambar. The completion of such debarring process results in each of the leads 150 defining an outer, distal end which is exposed in and substantially flush with a side surface defined by the package body 1030.

In the semiconductor device 1000, the lands 640 are exposed in the bottom surface 1033 of the package body 1030, as are the land portions 161 of the leads 150. As a result, the lands 640 and the land portions 161 are capable of being mounted to the surface of an underlying substrate such as a printed circuit board through the use of, for example, a soldering technique. Electrical signals are routed between the lands 640, the leads 150 and the semiconductor die 710 by the corresponding conductive wires 720. As seen in FIG. 10A, portions of the auxiliary support bars 634 are exposed in the trenches 1031 and in the bottom surface 1033 of the package body 1030.

This disclosure provides exemplary embodiments of the present invention. The scope of the present invention is not limited by these exemplary embodiments. Numerous variations, whether explicitly provided for by the specification or implied by the specification, such as variations in structure, dimension, type of material and manufacturing process may be implemented by one of skill in the art in view of this disclosure.

What is claimed is:

1. A semiconductor device, comprising:
   a die pad;
   a plurality of first lands in spaced relation to the die pad, wherein each of the first lands has a first land first top recessed portion disposed on a first land first end distal to the die pad, and wherein each of the first lands has a first land second top recessed portion disposed on a first land second end proximate to the die pad;
   a plurality of second lands in spaced relation to the die pad, wherein each of the second lands has a second land first bottom recessed portion disposed on a second land first end distal to the die pad;
   a semiconductor die electrically coupled to the first and second lands; and
   a package body defining a bottom surface and a side surface, the package body at least partially encapsulating the first and second lands and the semiconductor die such that at least portions of the first and second lands are exposed in and substantially flush with the bottom surface of the package body, wherein:
   the first and second lands are positioned between the die pad and the side surface;
   the second lands are positioned proximate to the side surface;
   the first lands are positioned between the die pad and the second lands; and
   the first land first recessed top portion of each first land and the second land first bottom recessed portion of each second land are encapsulated by the package body.

2. The semiconductor device of claim 1, wherein each of the second lands has a second land second bottom recessed portion disposed on a second land second end proximate to the die pad.

3. The semiconductor device of claim 1, wherein:
   the die pad has multiple peripheral edge segments;
   the semiconductor die is coupled to the die pad;
   the plurality of first lands are segregated into at least two sets extending along respective ones of at least two peripheral edge segments of the die pad;
   the plurality of second lands are segregated into at least two sets extending along respective ones of at least two peripheral edge segments of the die pad; and
   the semiconductor device further comprises a plurality of third lands segregated into at least two sets extending along respective ones of at least two peripheral edge segments of the die pad in spaced relation thereto, wherein:
   each of the third lands has a third land first top recessed portion disposed on a third land first end proximate to the die pad; and
   the third land first top recessed portion of each third land is encapsulated by the package body.

4. The semiconductor device of claim 3, wherein the first lands are separated from the third lands by at least one trench formed in the bottom surface of the package body.

5. The semiconductor device of claim 3 further comprising:
   a plurality of fourth lands segregated into at least two sets extending along respective ones of at least two peripheral edge segments of the die pad in spaced relation thereto, wherein:
   each of the fourth lands has a fourth land first bottom recessed portion disposed on a fourth land first end distal to the die pad; and
   the fourth lands are generally concentrically positioned between the second lands and the third lands.

6. The semiconductor device of claim 5, wherein each of the fourth lands has a fourth land second bottom recessed portion disposed on fourth land second end proximate to the die pad.

7. The semiconductor device of claim 3, wherein:
   the first lands are generally concentrically positioned between the third lands and the die pad such that each set of the first lands extends along a corresponding set of the third lands; and
   the third lands are generally concentrically positioned between the second lands and the first lands such that each set of the third lands extends along a corresponding set of the second lands.

8. The semiconductor device of claim 7, wherein the first lands of each set thereof are offset relative to the third lands of the corresponding set thereof.

9. The semiconductor device of claim 1 further comprising:
   a tie bar comprising an inner portion and an outer portion separated from the inner portion by a gap, the inner portion attached to and extending from the die pad, the tie bar having a tie bar top surface and a tie bar bottom surface, wherein:
   the tie bar top surface of the outer portion is co-planar with the die pad top surface;
   a first portion of the tie bar bottom surface of the outer portion comprises a recessed surface that is half-etched; and
   the first portion of the tie bar bottom surface is encapsulated by the package body.

10. The semiconductor device of claim 9, wherein:
    the die pad has a generally quadrangular configuration;
    the first and second lands are segregated into at least four sets that each extend along a respective one of the peripheral edge segments of the die pad; and
    a second portion of the tie bar bottom surface is co-planar with the die pad bottom surface and exposed in and substantially flush with the bottom surface of the package body.

11. The semiconductor device of claim 1, wherein a portion of the die pad is exposed in and substantially flush with the bottom surface of the package body.

12. The semiconductor device of claim 1, wherein the semiconductor die is electrically connected to the first and second lands by conductive wires which are covered by the package body.

13. A semiconductor device, comprising:
    a generally planar die pad;

a plurality of first lands extending along peripheral edge segments of the die pad in spaced relation thereto, wherein each of the first lands has a first land first top recessed portion disposed on a first land first end distal to the die pad;

a plurality of second lands extending along peripheral edge segments of the die pad in spaced relation thereto, wherein each of the second lands has a second land first bottom recessed portion disposed on a second land first end distal to the die pad;

a semiconductor die electrically coupled to the first and second lands; and a package body defining a generally planar bottom surface and a side surface, the package body at least partially encapsulating the first and second lands and the semiconductor die such that at least portions of the first and second lands are exposed in the bottom surface of the package body, wherein:

the first and second lands are positioned between the die pad and the side surface of the package body;

the second lands are positioned proximate to the side surface;

the first lands are positioned between the die pad and the second lands such that no portion of the first lands are positioned proximate to the side surface; and the first land first recessed portion of each first land and the second land first bottom recessed portion of each second land are encapsulated by the package body.

14. The semiconductor device of claim 13 further comprising:

a plurality of third lands extending along peripheral edge segments of the die pad in spaced relation thereto, wherein each of the third lands has a third land first top recessed portion disposed on a third land first end proximate to the die pad, wherein:

the third land first top recessed portion of each third land is encapsulated by the package body;

the semiconductor die is electrically coupled to the third lands; and the first lands are generally concentrically positioned between the third lands and the die pad, and the third lands are generally concentrically positioned between the second lands and the first lands.

15. The semiconductor device of claim 14, wherein:

each of the first lands has a first land second top recessed portion disposed on a first land second end proximate to the die pad; and each of the second lands has a second land second bottom recessed portion disposed on a second land second end proximate to the die pad.

16. The semiconductor device of claim 14 further comprising:

a plurality of fourth lands extending along peripheral edge segments of the die pad in spaced relation thereto, wherein:

each of the fourth lands has a fourth land first bottom recessed portion disposed on a fourth land first end distal to the die pad; and the fourth lands are generally concentrically positioned between the second lands and the third lands.

17. The semiconductor device of claim 16, wherein each of the fourth lands has a fourth land second bottom recessed portion disposed on fourth land second end proximate to the die pad.

18. The semiconductor device of claim 17, wherein:

the plurality of first lands and the plurality of third are offset relative to each other; and the plurality of second lands and the plurality of fourth lands are offset relative to each other.

19. The semiconductor device of claim 13 further comprising:

a tie bar comprising an inner linear portion and an outer linear portion separated from the inner linear portion by a gap, wherein:

the inner linear portion is attached to and extends from the die pad, the outer linear portion has a bottom surface with a first portion that is generally co-planar to a bottom surface of the die pad and a second portion that is recessed such that the second portion is recessed relative to the first portion; and the second portion of the bottom surface of the tie bar is encapsulated by the package body.

20. A semiconductor device, comprising:

a semiconductor die defining multiple peripheral edge segments;

a plurality of first lands segregated into at least two sets extending along respective ones of at least two peripheral edge segments of the semiconductor die, wherein each of the first lands has a first land first top recessed portion disposed on a first land first end distal to the die pad;

a plurality of second lands segregated into at least two sets extending along respective ones of at least two peripheral edge segments of the semiconductor die, wherein each of the second lands has a second land first top recessed portion disposed on a second land first end proximate to the die pad;

a plurality of third lands segregated into at least two sets extending along respective ones of at least two peripheral edge segments of the semiconductor die, wherein each of the third lands has a third land first bottom recessed portion disposed on a third land first end distal to the die pad; and a package body defining a generally planar bottom surface and a side surface, the package body at least partially encapsulating the first, second, and third lands and the semiconductor die such that at least portions of the first, second, and third lands are exposed in and substantially flush with the bottom surface of the package body, wherein:

the semiconductor die is electrically coupled to the first, second, and third lands;

at least the second and third lands are positioned between the semiconductor die and the side surface of the package body; and the first land first recessed portion of each first land, the second land first top recessed portion of each second land, and the third land first bottom recessed portion of each third land are encapsulated by the package body.

* * * * *